(12) United States Patent
Bettiol et al.

(10) Patent No.: US 10,526,568 B2
(45) Date of Patent: Jan. 7, 2020

(54) CLEANING COMPOSITION

(71) Applicant: The Procter & Gamble Company, Cincinnati, OH (US)

(72) Inventors: Jean-Luc Philippe Bettiol, Etterbeek (BE); Denis Alfred Gonzales, Brussels (BE); Juan Esteban Velasquez, Cincinnati, OH (US); Nicholas William Geary, Mariemont, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/188,651

(22) Filed: Nov. 13, 2018

(65) Prior Publication Data

US 2019/0144798 A1 May 16, 2019

(30) Foreign Application Priority Data

Nov. 13, 2017 (EP) ..................................... 17201317
Jun. 25, 2018 (EP) ..................................... 18179452

(51) Int. Cl.
| | | |
|---|---|---|
| *C07K 1/00* | (2006.01) | |
| *C11D 9/40* | (2006.01) | |
| *C11D 3/386* | (2006.01) | |
| *C07K 14/32* | (2006.01) | |

(52) U.S. Cl.
CPC ................ *C11D 9/40* (2013.01); *C07K 14/32* (2013.01); *C11D 3/386* (2013.01)

(58) Field of Classification Search
CPC ........................................................ C11D 9/40
See application file for complete search history.

(56) References Cited

U.S. PATENT DOCUMENTS 7,494,798 B2 * 2/2009 Berka ................... C07K 14/32
435/209
2017/0267730 A1 9/2017 Mcphee

FOREIGN PATENT DOCUMENTS

WO WO0071658 A1 11/2000

OTHER PUBLICATIONS

Search Report; Application No. 18179452.0-1105; dated Feb. 12, 2009; 8 pages.

* cited by examiner

*Primary Examiner* — Albert M Navarro
(74) *Attorney, Agent, or Firm* — Melissa G. Krasovec

(57) ABSTRACT

The present invention is directed to a cleaning composition including one or more Class III or Class IV BslA (Biofilm surface layer A) proteins and a surfactant system including one or more anionic surfactants and one or more co-surfactants, in a weight of ratio of less than 9:1. Methods of making and using such compositions are also provided.

18 Claims, 5 Drawing Sheets

Specification includes a Sequence Listing.

CLEANING COMPOSITION

REFERENCE TO A SEQUENCE LISTING

This application contains Sequence Listings in computer readable form. The computer readable form is incorporated herein by reference.

FIELD OF THE INVENTION

The present invention relates to a cleaning composition comprising one or more Class III or Class IV BslA (Biofilm surface layer A) proteins and a specific surfactant system. The composition provides one or more benefits, including good cleaning particularly good grease emulsification, long lasting suds especially in presence of greasy soils and surface modification that can contribute to second time cleaning benefits, improved drying, improved shine in the case of dishware.

BACKGROUND OF THE INVENTION

Cleaning compositions should provide good soil and/or grease cleaning while presenting a good suds profile in particular a long lasting suds profile especially in the presence of greasy soils. Users usually see suds as an indicator of the performance of the cleaning composition. Moreover, the user of a cleaning composition may also use the suds profile and the appearance of the suds (e.g., density, whiteness) as an indicator that the wash solution still contains active cleaning ingredients. This is particularly the case for manual washing, also referred to herein as hand-washing, where the user usually doses the cleaning composition depending on the suds remaining and renews the wash solution when the suds subsides or when the suds does not look thick enough. Thus, a cleaning composition, particularly a manual wash cleaning composition that generates little or low density suds would tend to be replaced by the user more frequently than is necessary. Accordingly, it is desirable for a cleaning composition to provide "good sudsing profile", which includes good suds height and/or density as well as good suds duration during the initial mixing of the composition with water and/or during the entire washing operation.

Several families of natural surface active proteins are able to aid suds performance in aqueous solutions (see Cooper, A., et al. (2017), *Colloids Surf, A: Physiochemical and Engineering Aspects*; Schor, M., et al. (2016), *Trends Biochem. Sci.* 41(7): 610-620). In particular, Class I or Class II BslA (Biofilm surface layer A) proteins have been used as a stabilizer in synthetic multiphase products that include sudsing agents to prevent phase separation and improve the sudsing performance of the products in liquid during use (see US2017/267730 (University of Edinburgh)). However, the amount of sudsing generated by such class I or class II BslA proteins in cleaning formulations is limited. This challenge cannot be solved by simply increasing the Class I or Class II BslA concentration level in the composition. That is because while the Class I or Class II BslA proteins may perform well in isolation, their performance may degrade (noticeably) in the presence of surfactants that are typically present in cleaning compositions.

Accordingly, the need remains for an improved cleaning composition comprising BslA proteins which has a further improved sudsing profile, particularly at low BslA proteins concentrations in the cleaning compositions. The need also exists for an improved cleaning composition, when used in a manual-washing process, the composition should also provide a pleasant washing experience, i.e., good feel on the user's hands during the wash. The composition should also be easy to rinse. Further it is desirous that the improved cleaning composition is stable and will not phase separate, resulting in greater shelf-life of the product. It is also desirable that cleaning compositions provide surface modification, contributing to shine in the case of dishware, improved second time cleaning. There is also the desire to reduce the amount of surfactants without negatively impacting sudsing nor grease cleaning and emulsification profile. Thus, there is the need to find new compositions that improve cleaning, suds longevity and improved after cleaning benefits in hand washing conditions. The Applicant discovered that some or all of the above-mentioned needs can be at least partially fulfilled through the improved cleaning composition as described herein below.

SUMMARY OF THE INVENTION

The present invention meets one or more of these needs based on the surprising discovery that by formulating a cleaning composition comprising a one or more Class III or Class IV BslA proteins and a specific surfactant system, such a composition exhibits good sudsing profile, particularly desirable suds volume and/or sustained suds stabilization, especially in the presence of greasy soils. It also provides good grease cleaning and emulsification benefits and can also provide surface modifications facilitating next time cleaning benefit.

According to the present invention there is provided a cleaning composition comprising one or more BslA proteins and a specific surfactant system, wherein the BslA proteins are a Class III or a Class IV BslA protein. The Class III BslA protein has at least 50%, preferably at least 60%, preferably at least 70%, preferably at least 80%, preferably at least 85%, preferably at least 90%, preferably at least 95%, preferably at least 98% or even 100% amino acid identity as calculated over the entire length of a sequence aligned against the entire length of a wild-type protein sequence: *Thermoactinomyces vulgaris* BslA (SEQ ID NO: 6). The Class IV BslA protein has at least 50%, preferably at least 60%, preferably at least 70%, preferably at least 80%, preferably at least 85%, preferably at least 90%, preferably at least 95%, preferably at least 98% or even 100% amino acid identity as calculated over the entire length of a sequence aligned against the entire length of at least one wild-type protein selected from the group consisting of: *Bacillus licheniformis* BslA (SEQ ID NO: 7, SEQ ID NO: 8, SEQ ID NO: 9, SEQ ID NO: 10, and SEQ ID NO: 11), *B. glycinifermentans* BslA (SEQ ID NO: 12, SEQ ID NO: 13, SEQ ID NO: 14, and SEQ ID NO: 15), *B. sonorensis* BslA (SEQ ID NO: 16), *B. paralicheniformis* BslA (SEQ ID NO: 17, and SEQ ID NO: 18), and *Bacillus* sp. BslA (SEQ ID NO: 19, SEQ ID NO: 20, SEQ ID NO: 21, and SEQ ID NO: 22). Surfactants can denature proteins but that does not seem to be the case in the composition of the invention with the Class III or Class IV BslA proteins.

Preferably the cleaning composition is a manual-washing cleaning composition. Preferably the cleaning composition is for manual dishwashing. Preferred compositions are in the form of a liquid.

The composition of the invention provides good cleaning and good suds profile, especially in the presence of greasy soils. It can also provide surface modifications facilitating next time cleaning benefit.

According to the present invention, there is provided a method of manual washing comprising the step of: delivering the cleaning composition as claimed to a volume of water and immersing soiled articles preferably dishware in the water. When the composition of the invention is used according to this method a good sudsing profile, with a long lasting effect is achieved.

In another aspect, the present invention is directed to a method of manually washing dishware comprising the steps of delivering a cleaning composition of the invention into a volume of water to form a wash solution and immersing the dishware in the solution.

In yet another aspect, the present invention relates to a method of manually washing dishware comprising: i) delivering a cleaning composition of the present invention onto the dishware or a cleaning implement; ii) cleaning the dishware with the composition in the presence of water; and iii) optionally, rinsing the dishware. Preferably, the composition of the present invention is used in neat form (i.e., direct application) since greater benefits in terms of grease cleaning are obtained when the composition is directly applied on the soiled surface or on a cleaning implement, such as a sponge, to be used to clean the soiled surface.

There is also provided the use of one or more BslA proteins, wherein the BslA proteins are a Class III BslA protein or a Class IV BslA protein as claimed to provide improved suds longevity and/or improved grease emulsification in an aqueous wash liquor during a washing process.

Preferably the manual washing is dishwashing and the soiled articles comprise soiled dishware. As used herein, "dishware" includes cookware and tableware.

The elements of the composition of the invention described in relation to the first aspect of the invention apply mutatis mutandis to the other aspects of the invention.

These and other features, aspects and advantages of the present invention will become evident to those skilled in the art from the detailed description which follows.

BRIEF DESCRIPTION OF THE DRAWINGS

While the specification concludes with claims particularly pointing out and distinctly claiming the invention, it is believed that the invention will be better understood from the following description of the accompanying figures:

DETAILED DESCRIPTION OF THE INVENTION

Definitions

Figure 1:
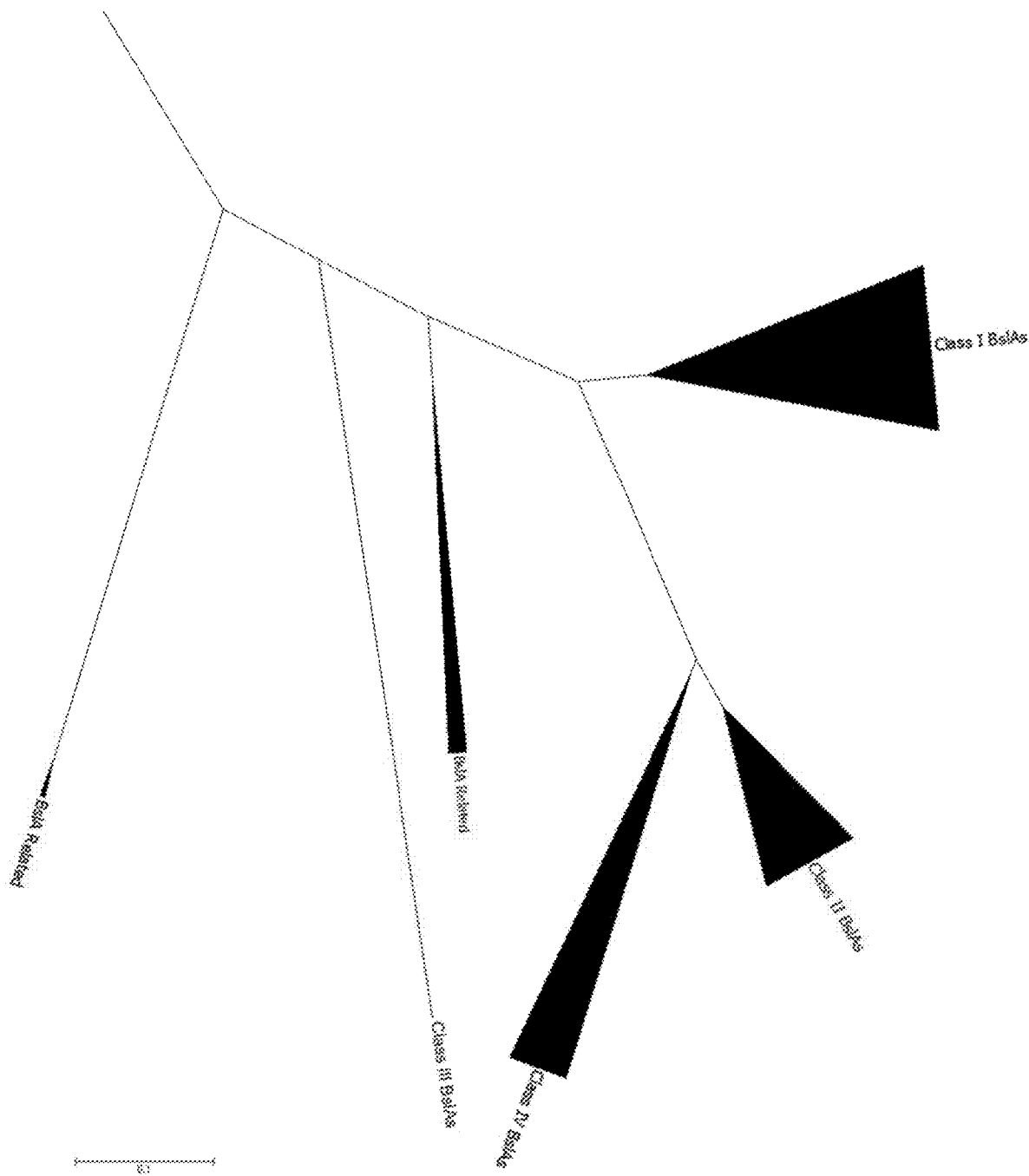
FIG. 1 is a phylogenetic tree of BslA proteins identifying four different classes. The tree was generated using NCBI BLASTp (https://blast.ncbi.nlm.nih.gov/Blast.cgi) and manipulated with MEGA6 Ver. 6.06 software.

As used herein, the articles "a" and "an" when used in a claim, are understood to mean one or more of what is claimed or described.

As used herein, the term "substantially free of" or "substantially free from" means that the indicated material is present in an amount of no more than 5 wt %, preferably no more than 2%, and more preferably no more than 1 wt % by weight of the composition.

As used therein, the term "essentially free of" or "essentially free from" means that the indicated material is present in an amount of no more than 0.1 wt % by weight of the composition, or preferably not present at an analytically detectable level in such composition. It may include compositions in which the indicated material is present only as an impurity of one or more of the materials deliberately added to such compositions.

As used herein, the term "amino acid identity" means the identity between two or more amino acid sequences and is expressed in terms of the identity or similarity between the sequences. Sequence identity can be measured in terms of percentage identity; the higher the percentage, the more identical the sequences are. The percentage identity is calculated over the length of comparison. For example, the amino acid identity is typically calculated over the entire length of a sequence aligned against the entire length of the reference sequence (e.g., SEQ ID NO: 6, SEQ ID NO: 7, etc.). Methods of alignment of sequences for comparison are well known in the art and identity can be calculated by many known methods. Various programs and alignment algorithms are described in the art. It should be noted that the terms 'sequence identity' and 'sequence similarity' can be used interchangeably.

As used herein, the term "BslA proteins" refers to the wild-type BslA proteins and variants thereof. The BslA proteins within the scope of the present invention are Class III or Class IV BslA proteins.

As used herein, the term "cleaning composition" refers to a composition or formulation designed for cleaning soiled surfaces. Such compositions include but are not limited to, dishwashing compositions, laundry detergent compositions, fabric softening compositions, fabric enhancing compositions, fabric freshening compositions, laundry pre-wash, laundry pretreat, laundry additives, spray products, dry cleaning agent or composition, laundry rinse additive, wash additive, post-rinse fabric treatment, ironing aid, hard surface cleaning compositions, unit dose formulation, delayed delivery formulation, detergent contained on or in a porous substrate or nonwoven sheet, and other suitable forms that may be apparent to one skilled in the art in view of the teachings herein. Such compositions may be used as a pre-cleaning treatment, a post-cleaning treatment, or may be added during the rinse or wash cycle of the cleaning process. The cleaning compositions may have a form selected from liquid, powder, single-phase or multi-phase unit dose or pouch form, tablet, gel, paste, bar, or flake. Preferably the composition is for manual-washing. Preferably, the cleaning composition of the present invention is a dishwashing detergent. Preferably the composition is in the form of a liquid.

As used herein the term "fragment" means an amino acid sequence of at least 20, 40, 60, 80, 100, 150 contiguous amino acids of the reference sequences or any integer there between.

As used herein the term "improved suds longevity" means an increase in the duration of visible suds in a washing process cleaning soiled articles using the composition comprising one or more Class III or Class IV BslA proteins, compared with the suds longevity provided by the same composition and process in the absence of the Class III or Class IV BslA proteins.

As used herein, the term "next time cleaning benefit" means the surface to be cleaned could be treated with a composition which would assist in easier removal of soil and/or stains during subsequent cleaning.

As used herein, the term "soiled surfaces" refers non-specifically to any type of flexible material consisting of a network of natural or artificial fibers, including natural, artificial, and synthetic fibers, such as, but not limited to, cotton, linen, wool, polyester, nylon, silk, acrylic, and the like, as well as various blends and combinations. Soiled surfaces may further refer to any type of hard surface, including natural, artificial, or synthetic surfaces, such as, but not limited to, tile, granite, grout, glass, composite, vinyl, hardwood, metal, cooking surfaces, plastic, and the like, as well as blends and combinations, as well as dishware. Key targeted soiled surfaces by this application are soiled dishware.

As used herein, the term "variant" of the BslA proteins means an amino acid sequence when the BslA protein is modified by, or at, one or more amino acids (for example 1, 2, 3, 4, 5, 6, 7, 8, 9 or 10 or more amino acid modifications) selected from substitutions, insertions, deletions and combinations thereof. The variant may have "conservative" substitutions, wherein a substituted amino acid has similar structural or chemical properties to the amino acid that replaces it, for example, replacement of leucine with isoleucine. A variant may have "non-conservative" changes, for example, replacement of a glycine with a tryptophan. Variants may also include sequences with amino acid deletions or insertions, or both. Guidance in determining which amino acid residues may be substituted, inserted, or deleted without abolishing the activity of the protein may be found using computer programs well known in the art. Variants may also include truncated forms derived from a wild type BslA protein, such as for example, a protein with a truncated N-terminus. Variants may also include forms derived by adding an extra amino acid sequence to a wild-type protein, such as for example, an N-terminal tag, a C-terminal tag or an insertion in the middle of the protein sequence.

As used herein, the term "water hardness" or "hardness" means uncomplexed cation ions (i.e., $Ca^{2+}$ or $Mg^{2+}$) present in water that have the potential to precipitate with anionic surfactants or other anionic actives in the cleaning composition under alkaline conditions, and thereby diminishing the surfactancy and cleaning capacity of surfactants. Further, the terms "high water hardness" and "elevated water hardness" can be used interchangeably and are relative terms for the purposes of the present invention, and are intended to include, but not limited to, a hardness level containing at least 12 grams of calcium ion per gallon water (gpg, "American grain hardness" units).

Cleaning Composition

A preferred cleaning composition is a manual dishwashing composition, preferably in liquid form. It typically contains from 30% to 95%, preferably from 40% to 90%, more preferably from 50% to 85% by weight of the composition of a liquid carrier in which the other essential and optional components are dissolved, dispersed or suspended. One preferred component of the liquid carrier is water.

Preferably the pH of the cleaning composition of the invention, measured as a 10% product concentration in demineralized water at 20° C., is adjusted to between 3 and 14, more preferably between 4 and 13, more preferably between 6 and 12 and most preferably between 8 and 10. The pH of the cleaning composition can be adjusted using pH modifying ingredients known in the art.

BslA Proteins

The cleaning composition in accordance with the present invention comprises one or more Class III or Class IV BslA proteins. Although BslA proteins have been referred to in the art as "bacterial hydrophobins", they have very little sequence or structural similarity to the well-characterized fungal hydrophobins (Linder, M. B. (2009), *Curr. Opin. Colloid Interface Sci.* 14(5): 356-363.), which are not part of the current invention.

BslA proteins exhibit structural and functional similarity to *Bacillus subtilis* YuaB, a protein previously identified and reported in the art (Kobayashi, K. and M. Iwano (2012), *Mol. Microbiol.* 85(1): 51-66.). BslA proteins contain an unusually large hydrophobic cap on the surface, which is essential for their activity in the formation of hydrophobic, non-wetting biofilms. They usually participate in biofilm assembly, forming surface layers around such biofilms.

A number of proteins from several bacterial classes, including Clostridia, Bacteroidia Actinobacteria, and Chlorobia, appear to be related to *B. subtilis* YuaB, but either do not conserve the hydrophobic cap or contain additional protein domains. Thus, these proteins are not expected to have functional similarity to *B. subtilis* YuaB. In the context of the current invention, proteins with sequence similarity to YuaB but with no hydrophobic cap or with additional protein domains are not classified as "BslA proteins".

The wild-type *B. subtilis* YuaB adopts a first conformation that is soluble in water, which transitions to a second conformation when adsorbed at an interface to expose hydrophobic residues to form the hydrophobic cap. This hydrophobic cap anchors YuaB protein at the interface between the phases by extending into the non-aqueous or non-polar phase. In addition, YuaB in the second configuration self-assembles to form a highly structured two-dimensional lattice at the interface. This two-dimensional lattice forms a viscoelastic film at the interface, which increases the stability of the interface, and resists rearrangement or relaxation of the interface after compression or deformation. Certain variants of wild-type YuaB, such as the L77K variant, do not retain the same ability as YuaB to form the highly structured two dimensional lattice at the interface, presumably as the mutation destabilizes the hydrophobic cap; it has significant interfacial activity, but does not form the same large-scale two-dimensional lattice as observed with the wild-type YuaB protein in which the hydrophobic cap is unaltered.

Figure 2:
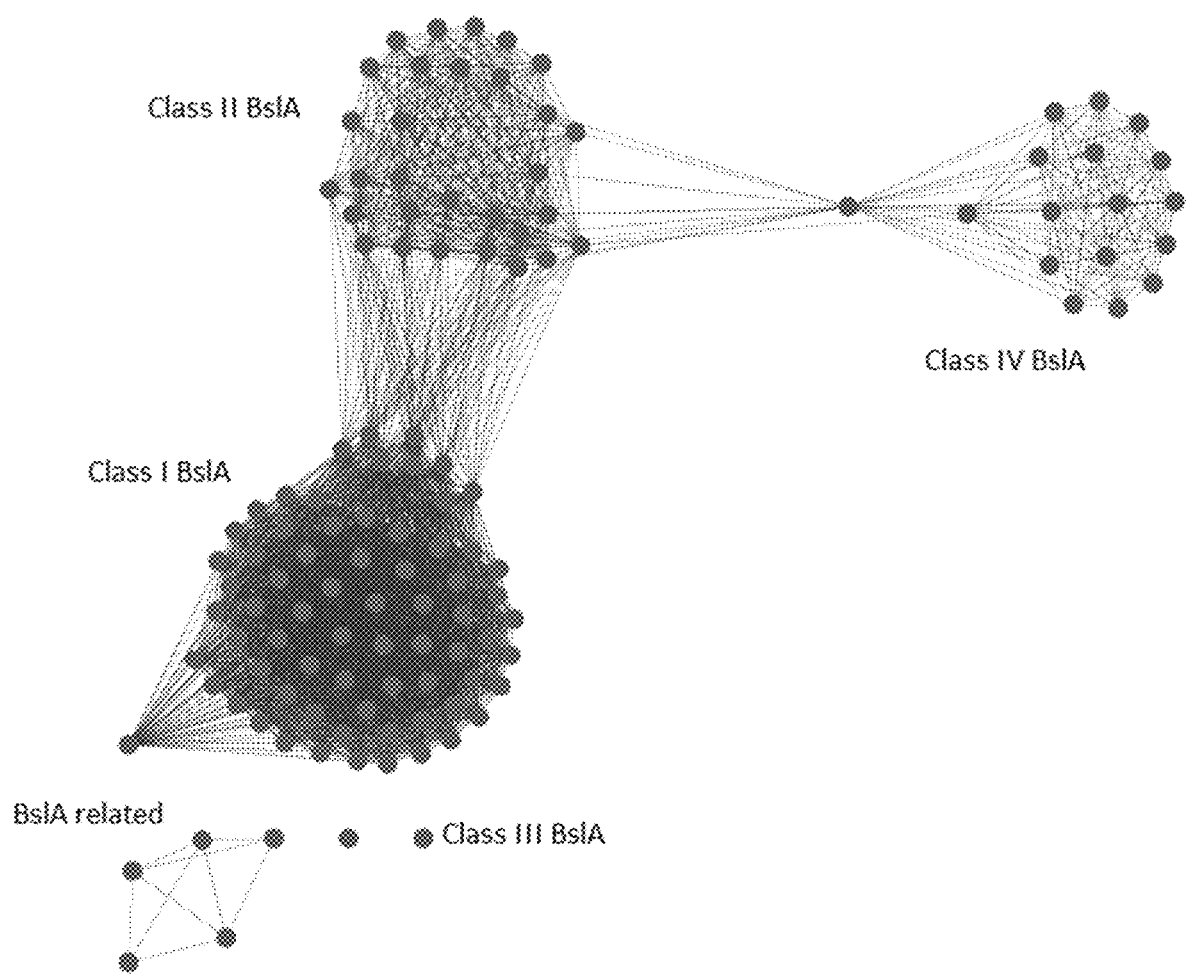
FIG. 2 is a sequence similarity network of BslA proteins identifying the four different classes. The network was generated using EFI—Enzyme Similarity Tool Ver 2.0 (http://efi.igb.illinois.edu/efi-est/).
Figure 3:
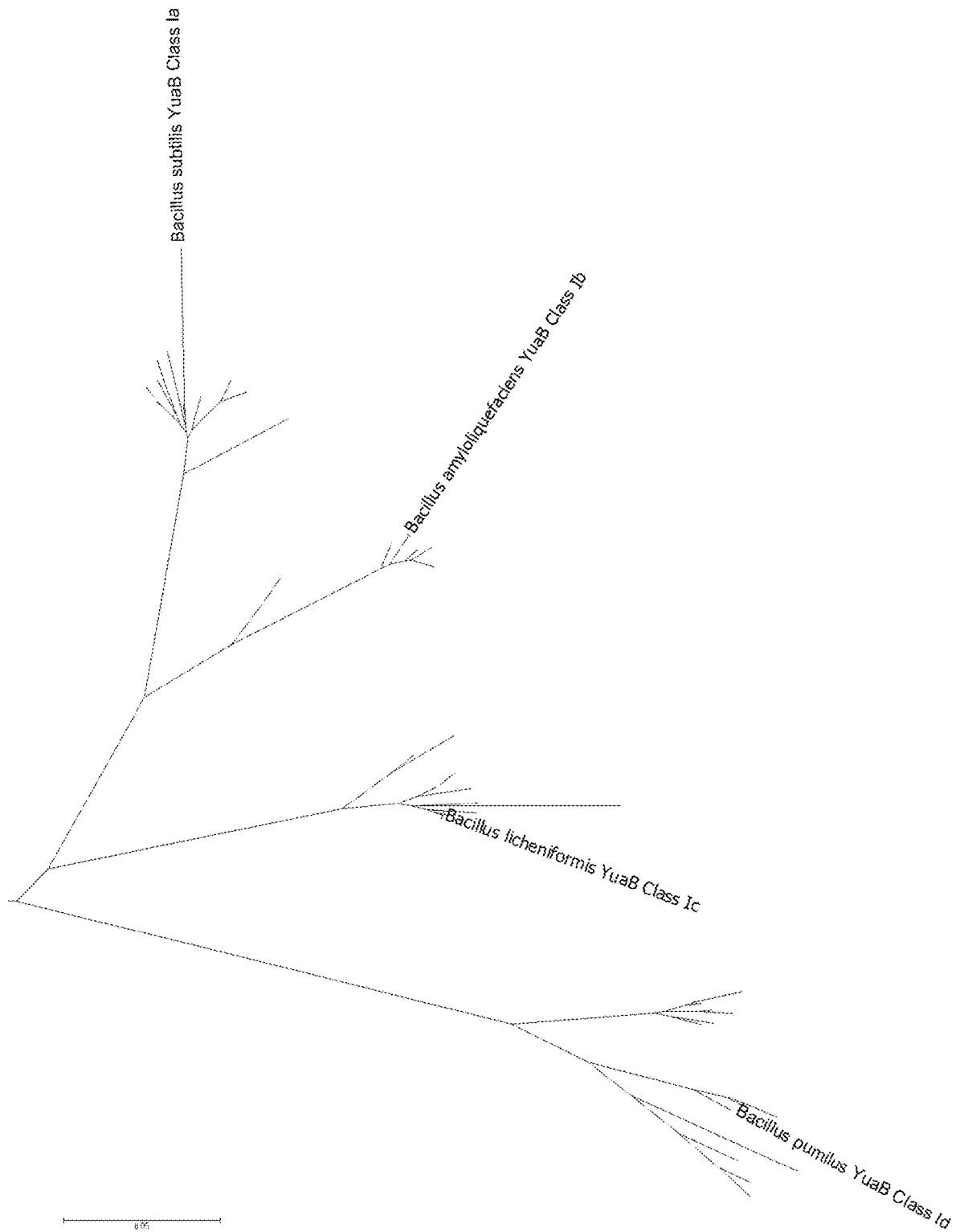
FIG. 3 is a phylogenetic tree of Class I BslA (YuaB-like) proteins, expanded from FIG. 1.
Figure 4:
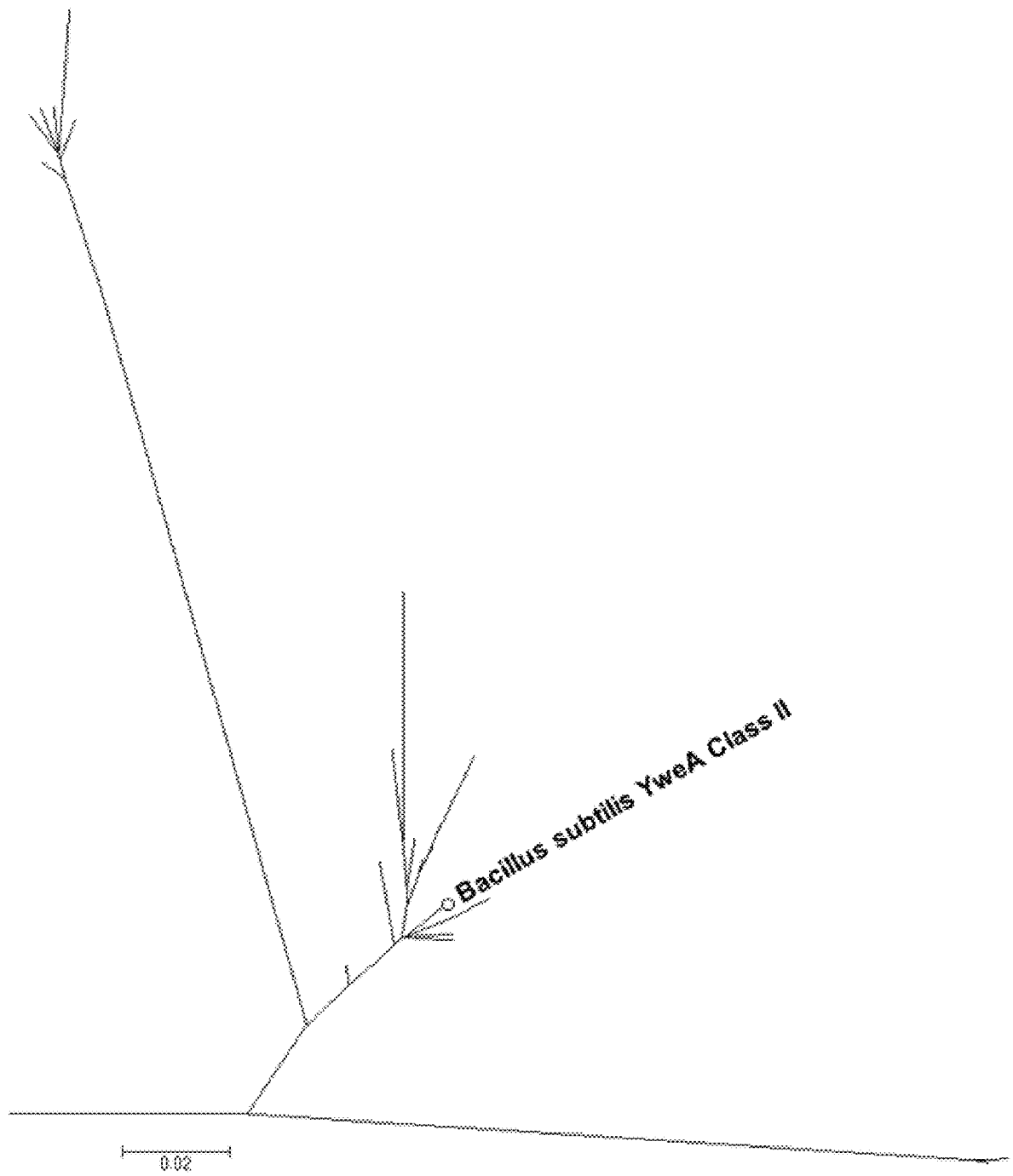
FIG. 4 is a phylogenetic tree of Class II BslA (YweA-like) proteins, expanded from FIG. 1.
Figure 5:
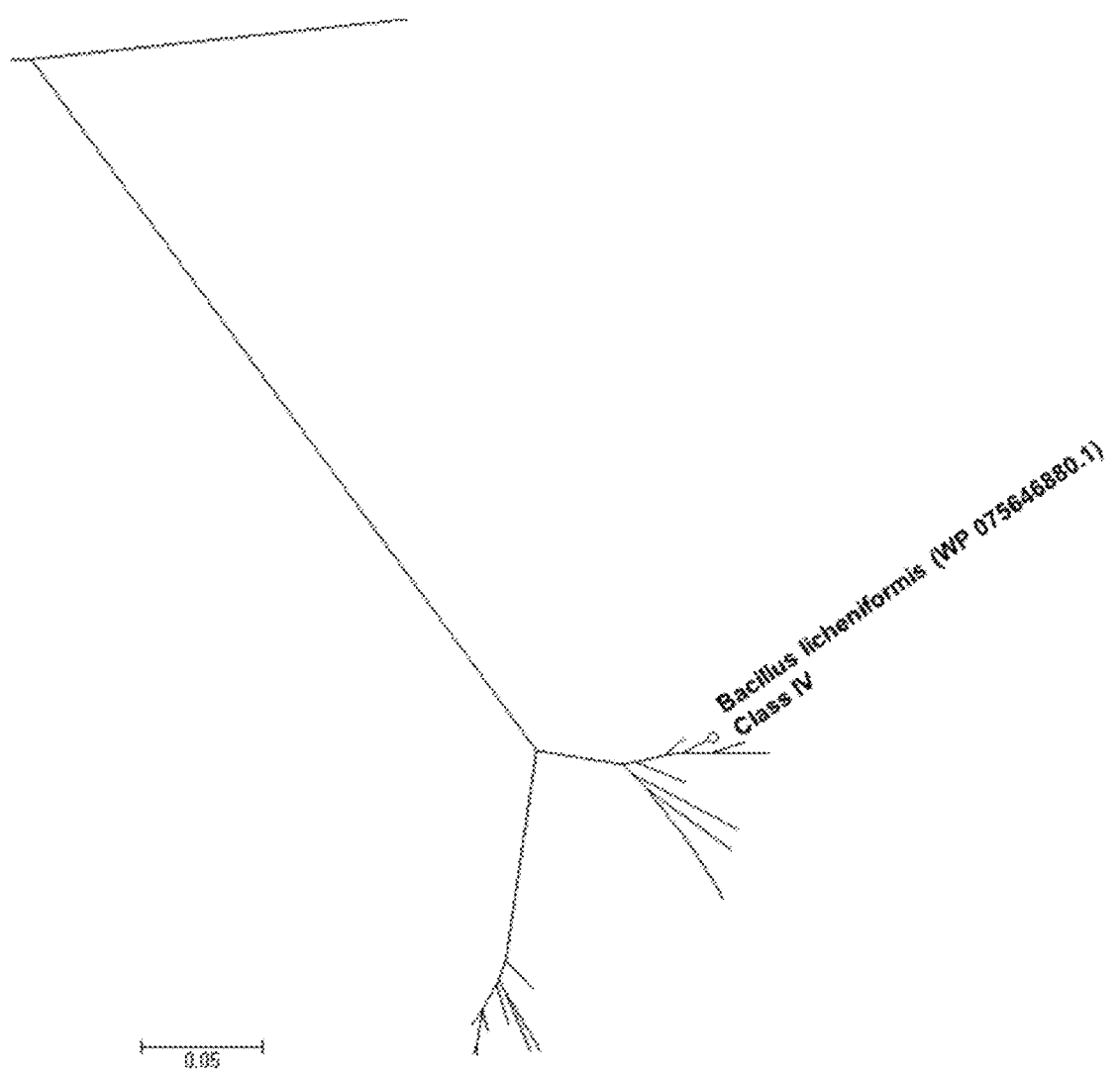
FIG. 5 is a phylogenetic tree of Class IV BslA proteins, expanded from FIG. 1.

All BslA proteins with hydrophobic caps that have been reported in the art are from the genus *Bacillus*. For example, *B. subtilis* YuaB (SEQ ID NO: 1), *B. licheniformis* YuaB (SEQ ID NO: 2), *B. amyloliquefaciens* YuaB (SEQ ID NO: 3), *B. pumilus* YuaB (SEQ ID NO: 4), and *B. subtilis* YweA (SEQ ID NO: 5) have been used in multiphasic systems (see WO2016027078). Based on phylogenetic analysis (see FIGS. 1, 2, 3 and 4), these BslA proteins can be classified as Class I BslA proteins (or YuaB-like) (SEQ ID NO: 1, SEQ ID NO: 2, SEQ ID NO: 3, and SEQ ID NO: 4) and Class II BslA proteins (or YweA-like) (SEQ ID NO: 5).

As part of the current invention, genome mining of NCBI protein databases using NCBI BLASTp searched with default parameters using the Advanced Search (found at http://www.ncbi.nih.gov/blast/) allowed the identification of several BslA proteins encoded by bacteria from different genera (such as *Thermoactinomyces* (SEQ ID NO: 6), *Jeotgalibacillus, Streptococcus*, and *Micobacterium*), demonstrating that BslA proteins with predicted hydrophobic caps are not exclusively produced by the genus *Bacillus*.

Furthermore, some of the identified proteins have low homology and less than 50% amino acid identity compared to the Class I BslA (YuaB-like) and Class II BslA (YweA-like) proteins and belong to two different phylogenetic groups, i.e. Class III BslA proteins with sequence similarity to *Thermoactinomyces vulgaris* BslA (SEQ ID NO: 6) and Class IV BslA proteins that include proteins from *B. licheniformis* (SEQ ID NOs: 7, 8, 9, 10, and 11), *B. glycinifermentans* (SEQ ID NOs: 12, 13, 14, and 15), *B. sonorensis* (SEQ ID NO: 16), *B. paralicheniformis* (SEQ ID NOs: 17, and 18), *Bacillus* sp. (SEQ ID NOs: 19, 20, 21, and 22), and *B. amyloliquefaciens*.

To our knowledge, only one member of Class III BslA proteins (SEQ ID NO: 6) has been deposited in protein sequence databases. This protein has an amino acid identity lower than 30% when compared to the Classes I, II, and IV BslA proteins described above.

In contrast, several examples of Class IV BslA proteins were identified by genome mining. These Class IV BslAs proteins (SEQ ID NOs: 7 to 22) have high homology at the C-terminus and a consensus sequence (SED ID NO: 23):

```
SNKEWXTSDIEXTYXPNXFVGXSXVEFXFPYRFHAXTRDXLNGXXLXYTQ
ILNDGQTVRVPVYAXSSSXFKLVMXRKTLPNAGTHXXTAELXXXGXXXXH
AEXXXXIXPR
``` wherein X represents any amino acid.

Unexpectedly, the Applicants found that, in comparison to Class I and II BslA proteins, Class III and Class IV BslA proteins are able to produce more sudsing in cleaning compositions comprising a specific surfactant system. Not wishing to be bound by theory, the Applicants believe that the increased sudsing benefits are due to differences in amino acid sequences and/or protein structures thereby enhancing the adsorption at the interface between two phases (oil/water or air/water).

Accordingly, a cleaning composition of the present invention comprises one or more BslA proteins, wherein the BslA proteins are a Class III or a Class IV BslA protein. The Class III BslA protein has at least 50%, preferably at least 60%, preferably at least 70%, preferably at least 80%, preferably at least 85%, preferably at least 90%, preferably at least 95%, preferably at least 98% or even 100% amino acid identity as calculated over the entire length of a sequence aligned against the entire length of a wild-type protein sequence: *Thermoactinomyces vulgaris* BslA (SEQ ID NO: 6). The Class IV BslA protein has at least 50%, preferably at least 60%, preferably at least 70%, preferably at least 80%, preferably at least 85%, preferably at least 90%, preferably at least 95%, preferably at least 98% or even 100% amino acid identity as calculated over the entire length of a sequence aligned against the entire length of at least one wild-type protein sequence selected from the group consisting of: *Bacillus licheniformis* BslA (SEQ ID NO: 7, SEQ ID NO: 8, SEQ ID NO: 9, SEQ ID NO: 10, and SEQ ID NO: 11), *B. glycinifermentans* BslA (SEQ ID NO: 12, SEQ ID NO: 13, SEQ ID NO: 14, and SEQ ID NO: 15), *B. sonorensis* BslA (SEQ ID NO: 16), *B. paralicheniformis* BslA (SEQ ID NO: 17, and SEQ ID NO: 18), and *Bacillus* sp. BslA (SEQ ID NO: 19, SEQ ID NO: 20, SEQ ID NO: 21, and SEQ ID NO: 22).

Preferably the cleaning composition of the present invention comprises one or more BslA proteins, wherein the BslA proteins are a Class III or a Class IV BslA protein, wherein the Class III BslA protein has at least 90%, preferably at least 95%, preferably at least 98% or even 100% amino acid identity as calculated over the entire length of a sequence aligned against the entire length of a wild-type protein: *Thermoactinomyces vulgaris* BslA (SEQ ID NO: 6), and wherein the Class IV BslA protein has at least 90%, preferably at least 95%, preferably at least 98% or even 100% amino acid identity as calculated over the entire length of a sequence aligned against the entire length of a wild-type protein sequence selected from the group consisting of: *B. licheniformis* BslA (SEQ ID NO: 7, SEQ ID NO: 8, SEQ ID NO: 9, SEQ ID NO: 10, and SEQ ID NO: 11), *B. glycinifermentans* BslA (SEQ ID NO: 12, SEQ ID NO: 13, SEQ ID NO: 14, and SEQ ID NO: 15), *B. sonorensis* BslA (SEQ ID NO: 16), *B. paralicheniformis* BslA (SEQ ID NO: 17, and SEQ ID NO: 18), and *Bacillus* sp. BslA (SEQ ID NO: 19, SEQ ID NO: 20, SEQ ID NO: 21, and SEQ ID NO: 22), preferably wherein the Class IV BslA protein preferably having at least 90%, preferably at least 95%, preferably at least 98% or even 100% amino acid identity as calculated over the entire length of a sequence aligned against the entire length of *B. licheniformis* BslA (SEQ ID NO: 7).

Preferably the cleaning composition of the present invention comprises one or more BslA proteins, wherein the BslA proteins are a Class IV BslA protein having at least 90%, preferably at least 95%, preferably at least 98% or even 100% amino acid identity as calculated over the entire length of a sequence aligned against the entire length of a protein having the amino acid sequence SEQ ID NO: 23.

The invention also includes variants in the form of truncated forms derived from a wild type BslA protein, such as a protein with a truncated N-terminus. Most of Class III or Class IV BslA proteins are predicted to include an N-terminal signal peptide that is likely removed upon secretion by the native organisms. The current invention may also include variants without the N-terminal signal peptide. For example, SEQ ID NO: 24, which corresponds to the sequence of full length wild-type *Thermoactinomyces vulgaris* BslA (SEQ ID NO: 6) without the predicted N-terminal signal peptide, is also part of the current invention. Bioinformatic tools, such as for example, signal peptide prediction server SignalP version 4.1 (Petersen T N., Brunak S., von Heijne G. and Nielsen H. (2011). *Nature Methods*, 8:785-786), can be used to predict the existence and length of such signal peptides. The invention also includes variants derived by adding an extra amino acid sequence to a wild-type protein, such as for example, an N-terminal tag, a C-terminal tag or an insertion in the middle of the protein sequence. Non-limiting examples of tags are maltose binding protein (MBP) tag, glutathione S-transferase (GST) tag, thioredoxin (Trx) tag, His-tag, and any other tags known by those skilled in art. Tags can be used to improve solubility and expression levels during fermentation or as a handle for enzyme purification.

Preferably the cleaning composition of the present invention comprises one or more BslA proteins, wherein the BslA proteins is a Class IV BslA protein having at least 90%, preferably at least 95%, preferably at least 98% or even 100% amino acid identity as calculated over the entire length of a sequence aligned against the entire length of a protein having the amino acid sequence SED ID NO: 24.

It is important that variants of Class III or Class IV BslA proteins retain or even improve the ability of the wild-type proteins to adsorb at an interface and to stabilize that interface. Some performance drop in a given property of Class III or Class IV BslA protein variants may of course be tolerated, but the Class III or Class IV BslA protein variants should retain suitable properties for the relevant application for which they are intended. For instance, screening of variants of one of the wild-types can be used to identify whether they retain appropriate properties.

Suitable examples of Class III or Class IV BslA protein variants include one conservative substitution in the peptide, such as a conservative substitution in SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, or SEQ ID NO: 22.

Other suitable examples of Class III or Class IV BslA protein variants include 10 or fewer conservative substitutions in the peptide, such as five or fewer. The Class III or Class IV BslA proteins of the invention may therefore include 1, 2, 3, 4, 5, 6, 7, 8, 9, 10 or more conservative substitutions. The Class III or Class IV BslA proteins can be produced to contain one or more conservative substitutions by manipulating the nucleotide sequence that encodes them using, for example, standard procedures such as site-directed mutagenesis or PCR. Alternatively, the Class III or Class IV BslA proteins can be produced to contain one or more conservative substitutions by using peptide synthesis methods, for example, as known in the art.

Examples of amino acids which may be substituted for an original amino acid in a Class III or Class IV BslA protein and which are regarded as conservative substitutions include: Ser for Ala; Lys for Arg; Gln or His for Asn; Glu for Asp; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

The Class III or Class IV BslA proteins of the invention may comprise variants of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, or SEQ ID NO: 22, wherein a short amino acid sequence containing two cysteine residues is added at the C-terminus. These cysteine residues can allow the Class III or Class IV BslA protein variants to form multimers (i.e., dimers, tetramers, hexamers and potentially higher order oligomers) in solution due to the formation of disulfide bonds between the cysteine residues of adjacent Class III or Class IV BslA protein variants.

The Class III or Class IV BslA proteins of the invention may also cover any fragments of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, or SEQ ID NO: 22. Preferably the Class III or Class IV BslA protein fragments can adsorb to an interface and stabilize that interface.

The Class III or Class IV BslA proteins can be modified by a variety of chemical techniques to produce derivatives having essentially the same or even improved activity as the unmodified peptides, and optionally having other desirable properties. For example, carboxylic acid groups of the protein, whether carboxyl-terminal or side chain, may be provided in the form of a salt of a pharmaceutically-acceptable cation or esterified, for example to form a C1-C6 alkyl ester, or converted to an amide, for example of formula $CONR_1R_2$ wherein $R_1$ and $R_2$ are each independently H or C1-C6 alkyl, or combined to form a heterocyclic ring, such as a 5- or 6-membered ring Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to C1-C6 alkyl or dialkyl amino or further converted to an amide. Hydroxyl groups of the peptide side chains may be converted to alkoxy or ester groups, for example C1-C6 alkoxy or C1-C6 alkyl ester, using well-recognized techniques. Phenyl and phenolic rings of the peptide side chains may be substituted with one or more halogen atoms, such as F, Cl, Br or I, or with C1-C6 alkyl, C1-C6 alkoxy, carboxylic acids and esters thereof, or amides of such carboxylic acids. Methylene groups of the peptide side chains can be extended to homologous C2-C4 alkylenes. Thiols can be protected with any one of a number of well-recognized protecting groups, such as acetamide groups. Those skilled in the art will also recognize methods for introducing cyclic structures into the BslA proteins of the present invention to select and provide conformational constraints to the structure that result in enhanced stability.

Identity, or homology, percentages as mentioned herein in respect of the present invention are those that can be calculated with the GAP program, obtainable from GCG (Genetics Computer Group Inc., Madison, Wis., USA). Alternatively, a manual alignment can be performed.

For polypeptide sequence comparison the following settings can be used: Alignment algorithm: Needleman and Wunsch, *J. Mol. Biol.* 1970, 48: 443-453. As a comparison matrix for amino acid similarity the Blosum62 matrix is used (Henikoff S. and Henikoff J. G., *P.N.A.S.* USA 1992, 89: 10915-10919). The following gap scoring parameters are used: Gap penalty: 12, gap length penalty: 2, no penalty for end gaps.

A given sequence is typically compared against the full-length sequence of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, or SEQ ID NO: 22 to obtain a score.

Preferably, the BslA proteins are present in an amount of from 0.01 wt % to 5 wt %, preferably from 0.1 wt % to 1 wt %, by weight of the cleaning composition, based on active protein, wherein the BslA proteins are selected from Class III or Class IV BslA proteins. The Class III BslA protein has at least 50%, preferably at least 60%, preferably at least 70%, preferably at least 80%, preferably at least 85%, preferably at least 90%, preferably at least 95%, preferably at least 98% or even 100% amino acid identity as calculated over the entire length of a sequence aligned against the entire length of a wild-type protein: *Thermoactinomyces vulgaris* BslA (SEQ ID NO: 6), and the Class IV BslA protein has at least 50%, preferably at least 60%, preferably at least 70%, preferably at least 80%, preferably at least 85%, preferably at least 90%, preferably at least 95%, preferably at least 98% or even 100% amino acid identity as calculated over the entire length of a sequence aligned against the entire length of a wild-type protein: *Bacillus licheniformis* BslA (SEQ ID NO: 7). More preferably the Class III BslA protein has at least 90%, preferably at least 95%, preferably at least 98% or even 100% amino acid identity as calculated over the entire length of a sequence aligned against the entire length of a wild-type protein: *Thermoactinomyces vulgaris* BslA (SEQ ID NO: 6), and the Class IV BslA protein has at least 90%, preferably at least 95%, preferably at least 98% or even 100% amino acid identity as calculated over the entire length of a sequence aligned against the entire length of at least one wild-type protein sequence selected from the group consisting of: *B. licheniformis* BslA (SEQ ID NO: 7, SEQ ID NO: 8, SEQ ID NO: 9, SEQ ID NO: 10, and SEQ ID NO: 11), *B. glycinifermentans* BslA (SEQ ID NO: 12, SEQ ID NO: 13, SEQ ID NO: 14, and SEQ ID NO: 15), *B. sonorensis* BslA (SEQ ID NO: 16), *B. paralicheniformis* BslA (SEQ ID NO: 17, and SEQ ID NO: 18), and *Bacillus* sp. BslA (SEQ ID NO: 19, SEQ ID NO: 20, SEQ ID NO: 21, and SEQ ID NO: 22), the Class IV BslA protein most preferably having at least 90%, preferably at least 95%, preferably at least 98% or even 100% amino acid identity to *B. licheniformis* BslA (SEQ ID NO: 7)

Surfactant System

Preferably the detergent composition of the invention comprises from 1% to 60%, preferably from 5% to 50%, more preferably from 8% to 40%, by weight of the total composition of a specific surfactant system.

The surfactant system of the composition of the present invention comprises an anionic surfactant. Preferably, the surfactant system for the cleaning composition of the present invention comprises from 1% to 40%, preferably 6% to 35%, more preferably 8% to 30% by weight of the total composition of an anionic surfactant. The anionic surfactant can be any anionic cleaning surfactant, preferably selected from sulfate and/or sulfonate anionic surfactants. HLAS (linear alkylbenzene sulfonate) would be the most preferred sulfonate anionic surfactant. Especially preferred anionic surfactant is selected from the group consisting of alkyl sulfate, alkyl alkoxy sufate and mixtures thereof, and preferably wherein the alkyl alkoxy sulfate is an alkyl ethoxy sulfate. Preferred anionic surfactant is a combination of alkyl sulfates and alkyl ethoxy sulfates with a combined mol average ethoxylation degree of less than 5, preferably less than 3, more preferably less than 2 and more than 0.5 and an average level of branching of from 5% to 40%, more preferably from 10% to 35%, and even more preferably from 20% to 30%.

The average alkoxylation degree is the mol average alkoxylation degree of all the components of the mixture (i.e., mol average alkoxylation degree) of the anionic surfactant. In the mol average alkoxylation degree calculation the weight of sulfate anionic surfactant components not having alkoxylate groups should also be included.

Mol average alkoxylation degree=($x1$*alkoxylation degree of surfactant 1+$x2$*alkoxylation degree of surfactant 2+ . . . )/($x1$+$x2$+ . . . )

wherein x1, x2, . . . are the number of moles of each sulfate anionic surfactant of the mixture and alkoxylation degree is the number of alkoxy groups in each sulfate anionic surfactant.

The average level of branching is the weight average % of branching and it is defined according to the following formula:

Weight average of branching (%)=[($x1$*wt % branched alcohol 1 in alcohol 1+$x2$*wt % branched alcohol 2 in alcohol 2+ . . . )/ ($x1$+$x2$+ . . . )]*100 wherein x1, x2, . . . are the weight in grams of each alcohol in the total alcohol mixture of the alcohols which were used as starting material for the anionic surfactant for the composition of the invention. In the weight average branching degree calculation the weight of anionic surfactant components not having branched groups should also be included.

Suitable examples of commercially available sulfates include, those based on Neodol alcohols ex the Shell company, Lial—Isalchem and Safol ex the Sasol company, natural alcohols ex The Procter & Gamble Chemicals company. Suitable sulfonate surfactants for use herein include water-soluble salts of C8-C18 alkyl or hydroxyalkyl sulfonates; C11-C18 alkyl benzene sulfonates (LAS), modified alkylbenzene sulfonate (MLAS); methyl ester sulfonate (MES); and alpha-olefin sulfonate (AOS). Those also include the paraffin sulfonates may be monosulfonates and/or disulfonates, obtained by sulfonating paraffins of 10 to 20 carbon atoms. The sulfonate surfactant also include the alkyl glyceryl sulfonate surfactants.

The surfactant system of the composition of the present invention further comprises a primary co-surfactant system, wherein the primary co-surfactant system is preferably selected from the group consisting of amphoteric surfactant, zwitterionic surfactant and mixtures thereof. Preferably, the surfactant system for the cleaning composition of the present invention comprises from 0.5% to 15%, preferably from 1% to 12%, more preferably from 2% to 10%, by weight of the total composition of a primary co-surfactant system.

Preferably the primary co-surfactant system is an amphoteric surfactant. Preferably, the primary co-surfactant system is an amine oxide surfactant, and wherein the composition comprises anionic surfactant and amine oxide surfactant in a ratio of less than 9:1, more preferably from 5:1 to 1:1, more preferably from 4:1 to 2:1, preferably from 3:1 to 2.5:1.

Preferred amine oxides are alkyl dimethyl amine oxide or alkyl amido propyl dimethyl amine oxide, more preferably alkyl dimethyl amine oxide and especially coco dimethyl amino oxide. Amine oxide may have a linear or branched alkyl moiety.

Preferably the amine oxide surfactant is a mixture of amine oxides comprising a low-cut amine oxide and a mid-cut amine oxide. The amine oxide of the composition of the invention then comprises:

a) from a 10% to 45% by weight of the amine oxide of low-cut amine oxide of formula R1R2R3AO wherein R1 and R2 are independently selected from hydrogen, C1-C4 alkyls or mixtures thereof, and R3 is selected from C10 alkyls or mixtures thereof; and b) from 55% to 90% by weight of the amine oxide of mid-cut amine oxide of formula R4R5R6AO wherein R4 and R5 are independently selected from hydrogen, C1-C4 alkyls or mixtures thereof, and R6 is selected from C12-C16 alkyls or mixtures thereof.

In a preferred low-cut amine oxide for use herein R3 is n-decyl. In another preferred low-cut amine oxide for use herein R1 and R2 are both methyl. In an especially preferred low-cut amine oxide for use herein R1 and R2 are both methyl and R3 is n-decyl.

Preferably, the amine oxide comprises less than 5%, more preferably less than 3%, by weight of the amine oxide of an amine oxide of formula R7R8R9AO wherein R7 and R8 are selected from hydrogen, C1-C4 alkyls and mixtures thereof and wherein R9 is selected from C8 alkyls and mixtures thereof. Compositions comprising R7R8R9AO tend to be unstable and do not provide very suds mileage.

Preferably the primary co-surfactant system is a zwitterionic surfactant. Suitable examples of zwitterionic surfactants include betaines, such as alkyl betaines, alkylamidobetaine, amidazoliniumbetaine, sulfobetaine (INCI Sultaines) as well as the Phosphobetaine and preferably meets formula (I):

R1-[CO—X(CH2)$n$]$x$-N+(R2)(R3)-(CH2)$m$-[CH(OH)—CH2]y-Y— (I)

wherein
R1 is a saturated or unsaturated C6-22 alkyl residue, preferably C8-18 alkyl residue, in particular a saturated C10-16 alkyl residue, for example a saturated C12-14 alkyl residue;
X is NH, NR4 with C1-4 Alkyl residue R4, O or S;
n is a number from 1 to 10, preferably 2 to 5, in particular 3;
x is 0 or 1, preferably 1;
R2 and R3 are independently a C1-4 alkyl residue, potentially hydroxy substituted such as a hydroxyethyl, preferably a methyl;
m is a number from 1 to 4, in particular 1, 2 or 3;
y 0 or 1; and
Y is COO, SO3, OPO(OR5)O or P(O)(OR5)O, whereby R5 is a hydrogen atom H or a C1-4 alkyl residue.

Preferred betaines are the alkyl betaines of the formula (Ia), the alkyl amido propyl betaine of the formula (Ib), the Sulfo betaines of the formula (Ic), and the Amido sulfobetaine of the formula (Id);

R1-N+(CH3)2-CH2COO— (Ia)

R1-CO—NH(CH2)3-N+(CH3)2-CH2COO— (Ib)

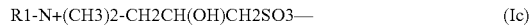

R1-N+(CH3)2-CH2CH(OH)CH2SO3— (Ic)

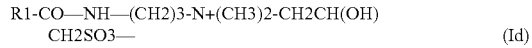

R1-CO—NH—(CH2)3-N+(CH3)2-CH2CH(OH)CH2SO3— (Id)

in which R1 has the same meaning as in formula (I). Particularly preferred betaines are the Carbobetaine [wherein Y—=COO—], in particular the Carbobetaine of the formula (Ia) and (Ib), more preferred are the Alkylamidobetaine of the formula (Ib). A preferred betaine is, for example, Cocoamidopropylbetaine.

Preferably the surfactant system of the composition of the present invention further comprises from 0.1% to 10% by weight of the total composition of a secondary co-surfactant system preferably comprising a non-ionic surfactant. Suitable non-ionic surfactants include the condensation products of aliphatic alcohols with from 1 to 25 moles of ethylene oxide. The alkyl chain of the aliphatic alcohol can either be straight or branched, primary or secondary, and generally contains from 8 to 22 carbon atoms. Particularly preferred are the condensation products of alcohols having an alkyl group containing from 10 to 18 carbon atoms, preferably from 10 to 15 carbon atoms with from 2 to 18 moles, preferably 2 to 15, more preferably 5-12 of ethylene oxide per mole of alcohol. Highly preferred non-ionic surfactants are the condensation products of guerbet alcohols with from 2 to 18 moles, preferably 2 to 15, more preferably 5-12 of ethylene oxide per mole of alcohol. Preferably, the non-ionic surfactants are an alkyl ethoxylated surfactants, preferably comprising from 9 to 15 carbon atoms in its alkyl chain and from 5 to 12 units of ethylene oxide per mole of alcohol. Other suitable non-ionic surfactants for use herein include fatty alcohol polyglycol ethers, alkylpolyglucosides and fatty acid glucamides, preferably alkylpolyglucosides. Preferably the alkyl polyglucoside surfactant is a C8-C16 alkyl polyglucoside surfactant, preferably a C8-C14 alkyl polyglucoside surfactant, preferably with an average degree of polymerization of between 0.1 and 3, more preferably between 0.5 and 2.5, even more preferably between 1 and 2. Most preferably the alkyl polyglucoside surfactant has an average alkyl carbon chain length between 10 and 16, preferably between 10 and 14, most preferably between 12 and 14, with an average degree of polymerization of between 0.5 and 2.5 preferably between 1 and 2, most preferably between 1.2 and 1.6. C8-C16 alkyl polyglucosides are commercially available from several suppliers (e.g., Simusol® surfactants from Seppic Corporation; and Glucopon® 600 CSUP, Glucopon® 650 EC, Glucopon® 600 CSUP/MB, and Glucopon® 650 EC/MB, from BASF Corporation). Preferably, the composition comprises the anionic surfactant and the non-ionic surfactant in a ratio of from 2:1 to 50:1, preferably 2:1 to 10:1.

Enzymes

Preferred compositions of the invention may comprise one or more enzymes selected from the group consisting of amylases, lipases, proteases, cellulases, lipoxygenases, diol synthases, and mixtures thereof. Each additional enzyme is typically present in an amount from 0.0001 wt % to 1 wt % (based on active protein) more preferably from 0.0005 wt % to 0.5 wt %, most preferably 0.005 wt % to 0.1 wt %, by weight of the cleaning composition.

Enzyme Stabilizer

When comprising enzymes preferably the composition of the invention comprises an enzyme stabilizer. Suitable enzyme stabilizers may be selected from the group consisting of (a) univalent, bivalent and/or trivalent cations preferably selected from the group of inorganic or organic salts of alkaline earth metals, alkali metals, aluminum, iron, copper and zinc, preferably alkali metals and alkaline earth metals, preferably alkali metal and alkaline earth metal salts with halides, sulfates, sulfites, carbonates, hydrogencarbonates, nitrates, nitrites, phosphates, formates, acetates, propionates, citrates, maleates, tartrates, succinates, oxalates, lactates, and mixtures thereof. In a preferred embodiment the salt is selected from the group consisting of sodium chloride, calcium chloride, potassium chloride, sodium sulfate, potassium sulfate, sodium acetate, potassium acetate, sodium formate, potassium formate, calcium lactate, calcium nitrate and mixtures thereof. Most preferred are salts selected from the group consisting of calcium chloride, potassium chloride, potassium sulfate, sodium acetate, potassium acetate, sodium formate, potassium formate, calcium lactate, calcium nitrate, and mixtures thereof, and in particular potassium salts selected from the group of potassium chloride, potassium sulfate, potassium acetate, potassium formate, potassium propionate, potassium lactate and mixtures thereof. Most preferred are potassium acetate and potassium chloride. Preferred calcium salts are calcium formate, calcium lactate and calcium nitrate including calcium nitrate tetrahydrate. Calcium and sodium formate salts may be preferred. These cations are present at at least 0.01 wt %, preferably at least 0.03 wt %, more preferably at least 0.05 wt %, most preferably at least 0.25 wt % up to 2 wt % or even up to 1 wt % by weight of the total composition. These salts are formulated from 0.1 to 5 wt %, preferably from 0.2 to 4 wt %, more preferably from 0.3 to 3 wt %, most preferably from 0.5 to 2 wt % relative to the total weight of the composition. Further enzyme stabilizers can be selected from the group (b) carbohydrates selected from the group consisting of oligosaccharides, polysaccharides and mixtures thereof, such as a monosaccharide glycerate as described in WO201219844; (c) mass efficient reversible protease inhibitors selected from the group consisting of phenyl boronic acid and derivatives thereof, preferably 4-formyl phenylboronic acid; (d) alcohols such as 1,2-propane diol, propylene glycol; (e) peptide aldehyde stabilizers such as tripeptide aldehydes such as Cbz-Gly-Ala-Tyr-H, or disubstituted alaninamide; (f) carboxylic acids such as phenyl alkyl dicarboxylic acid as described in WO2012/19849 or multiply substituted benzyl carboxylic acid comprising a carboxyl group on at least two carbon atoms of the benzyl radical such as described in WO2012/19848, phthaloyl glutamine acid, phthaloyl asparagine acid, aminophthalic acid and/or an oligoamino-biphenyl-oligocarboxylic acid; and; (g) mixtures thereof.

Salt

The composition of the present invention may optionally comprise from 0.01% to 3%, preferably from 0.05% to 2%, more preferably from 0.2% to 1.5%, or most preferably 0.5% to 1%, by weight of the total composition of a salt, preferably a monovalent, divalent inorganic salt or a mixture thereof, preferably sodium chloride. Most preferably the composition alternatively or further comprises a multivalent metal cation in the amount of from 0.01 wt % to 3 wt %, preferably from 0.05% to 2%, more preferably from 0.2% to 1.5%, or most preferably 0.5% to 1% by weight of said composition, preferably said multivalent metal cation is magnesium, aluminium, copper, calcium or iron, more preferably magnesium, most preferably said multivalent salt is magnesium chloride. Without wishing to be bound by theory, it is believed that use of a multivalent cation helps with the formation of protein/protein, surfactant/surfactant or hybrid protein/surfactant network at the oil water and air water interface that is strengthening the suds.

Carbohydrates

Preferably the composition of the present invention comprises one or more carbohydrates selected from the group comprising O-glycan, N-glycan, and mixtures thereof. Preferably the cleaning composition further comprises one or more carbohydrates selected from the group comprising derivatives of glucose, mannose, lactose, galactose, allose, altrose, gulose, idose, talose, fucose, fructose, sorbose, tagatose, psicose, arabinose, ribose, xylose, lyxose, ribulose, and xylulose. More preferably the cleaning composition comprises one or more carbohydrates selected from the group of α-glucans and β-glucans. Glucans are polysaccharides of D-glucose monomers, linked by glycosidic bonds. Non-limiting examples of α-glucans are dextran, starch, floridean starch, glycogen, pullulan, and their derivatives. Non-limiting examples of β-glucans are cellulose, chrysolaminarin, curdlan, laminarin, lentinan, lichenin, oat beta-glucan, pleuran, zymosan, and their derivatives.

Hydrotrope

The composition of the present invention may optionally comprise from 1% to 10%, or preferably from 0.5% to 10%, more preferably from 1% to 6%, or most preferably from 0.1% to 3%, or combinations thereof, by weight of the total composition of a hydrotrope, preferably sodium cumene sulfonate. Other suitable hydrotropes for use herein include anionic-type hydrotropes, particularly sodium, potassium, and ammonium xylene sulfonate, sodium, potassium and ammonium toluene sulfonate, sodium potassium and ammonium cumene sulfonate, and mixtures thereof, as disclosed in U.S. Pat. No. 3,915,903. Preferably the composition of the present invention is isotropic. An isotropic composition is distinguished from oil-in-water emulsions and lamellar phase compositions. Polarized light microscopy can assess whether the composition is isotropic. See e.g., *The Aqueous Phase Behaviour of Surfactants*, Robert Laughlin, Academic Press, 1994, pp. 538-542. Preferably an isotropic composition is provided. Preferably the composition comprises 0.1% to 3% by weight of the total composition of a hydrotrope, preferably wherein the hydrotrope is selected from sodium, potassium, and ammonium xylene sulfonate, sodium, potassium and ammonium toluene sulfonate, sodium potassium and ammonium cumene sulfonate, and mixtures thereof.

Organic Solvent

The composition of the present invention may optionally comprise an organic solvent. Suitable organic solvents include C4-14 ethers and diethers, polyols, glycols, alkoxylated glycols, C6-C16 glycol ethers, alkoxylated aromatic alcohols, aromatic alcohols, aliphatic linear or branched alcohols, alkoxylated aliphatic linear or branched alcohols, alkoxylated C1-C5 alcohols, C8-C14 alkyl and cycloalkyl hydrocarbons and halohydrocarbons, and mixtures thereof. Preferably the organic solvents include alcohols, glycols, and glycol ethers, alternatively alcohols and glycols. The composition comprises from 0% to less than 50%, preferably from 0.01% to 25%, more preferably from 0.1% to 10%, or most preferably from 0.5% to 5%, by weight of the total composition of an organic solvent, preferably an alcohol, more preferably an ethanol, a polyalkyleneglycol, more preferably polypropyleneglycol, and mixtures thereof.

Amphiphilic Polymer

The composition of the present invention may further comprise from 0.01% to 5%, preferably from 0.05% to 2%, more preferably from 0.07% to 1% by weight of the total composition of an amphiphilic polymer selected from the groups consisting of amphiphilic alkoxylated polyalkyleneimine and mixtures thereof, preferably an amphiphilic alkoxylated polyalkyleneimine.

Preferably, the amphiphilic alkoxylated polyalkyleneimine is an alkoxylated polyethyleneimine polymer comprising a polyethyleneimine backbone having average molecular weight range from 100 to 5,000, preferably from 400 to 2,000, more preferably from 400 to 1,000 Daltons and the alkoxylated polyethyleneimine polymer further comprising:

(i) one or two alkoxylation modifications per nitrogen atom by a polyalkoxylene chain having an average of 1 to 50 alkoxy moieties per modification, wherein the terminal alkoxy moiety of the alkoxylation modification is capped with hydrogen, a C1-C4 alkyl or mixtures thereof;

(ii) an addition of one C1-C4 alkyl moiety and one or two alkoxylation modifications per nitrogen atom by a polyalkoxylene chain having an average of 1 to 50 alkoxy moieties per modification wherein the terminal alkoxy moiety is capped with hydrogen, a C1-C4 alkyl or mixtures thereof; or (iii) a combination thereof; and wherein the alkoxy moieties comprises ethoxy (EO) and/or propxy (PO) and/or butoxy (BO) and wherein when the alkoxylation modification comprises EO it also comprises PO or BO.

Preferred amphiphilic alkoxylated polyethyleneimine polymers comprise EO and PO groups within their alkoxylation chains, the PO groups preferably being in terminal position of the alkoxy chains, and the alkoxylation chains preferably being hydrogen capped. Hydrophilic alkoxylated polyethyleneimine polymers solely comprising ethoxy (EO) units within the alkoxylation chain could also optionally be formulated within the scope of this invention.

For example, but not limited to, below is shown possible modifications to terminal nitrogen atoms in the polyethyleneimine backbone where R represents an ethylene spacer and E represents a C1-C4 alkyl moiety and X— represents a suitable water soluble counterion.

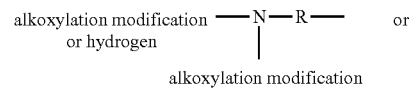

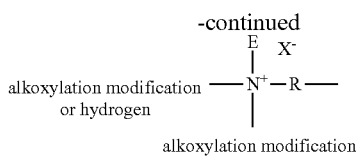

Also, for example, but not limited to, below is shown possible modifications to internal nitrogenatoms in the polyethyleneimine backbone where R represents an ethylene spacer and E represents a $C_1$-$C_4$ alkyl moiety and X— represents a suitable water soluble counterion.

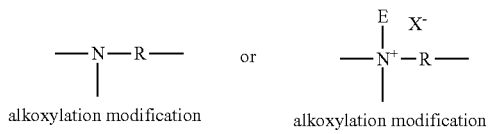

The alkoxylation modification of the polyethyleneimine backbone consists of the replacement of a hydrogen atom by a polyalkoxylene chain having an average of 1 to 50 alkoxy moieties, preferably from 20 to 45 alkoxy moieties, most preferably from 30 to 45 alkoxy moieties. The alkoxy moieties are selected from ethoxy (EO), propoxy (PO), butoxy (BO), and mixtures thereof. Alkoxy moieties solely comprising ethoxy units are outside the scope of the invention though. Preferably, the polyalkoxylene chain is selected from ethoxy/propoxy block moieties. More preferably, the polyalkoxylene chain is ethoxy/propoxy block moieties having an average degree of ethoxylation from 3 to 30 and an average degree of propoxylation from 1 to 20, more preferably ethoxy/propoxy block moieties having an average degree of ethoxylation from 20 to 30 and an average degree of propoxylation from 10 to 20.

More preferably the ethoxy/propoxy block moieties have a relative ethoxy to propoxy unit ratio between 3 to 1 and 1 to 1, preferably between 2 to 1 and 1 to 1. Most preferably the polyalkoxylene chain is the ethoxy/propoxy block moieties wherein the propoxy moiety block is the terminal alkoxy moiety block.

The modification may result in permanent quaternization of the polyethyleneimine backbone nitrogen atoms. The degree of permanent quaternization may be from 0% to 30% of the polyethyleneimine backbone nitrogen atoms. It is preferred to have less than 30% of the polyethyleneimine backbone nitrogen atoms permanently quaternized. Most preferably the degree of quaternization is 0%.

A preferred polyethyleneimine has the general structure of Formula (II):

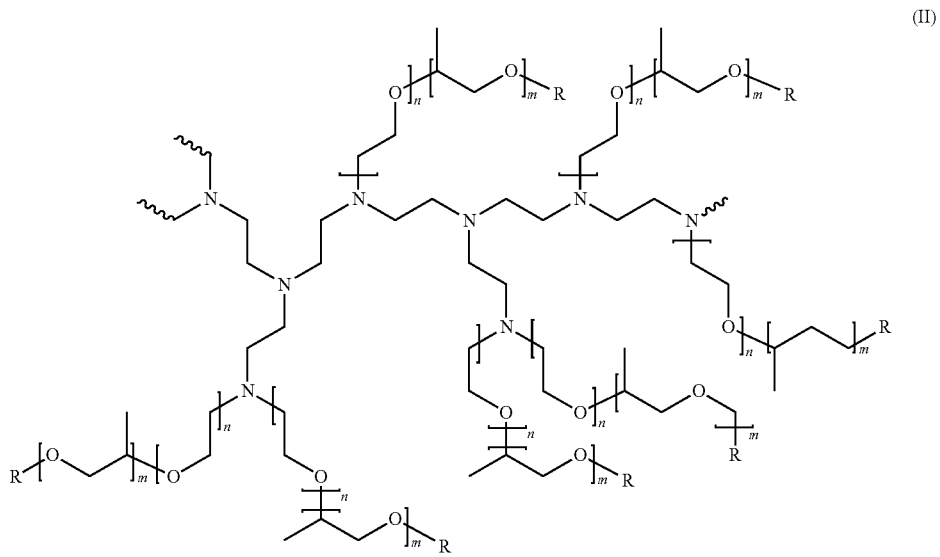

wherein the polyethyleneimine backbone has a weight average molecular weight of 600, n of formula (II) has an average of 10, m of formula (II) has an average of 7 and R of formula (II) is selected from hydrogen, a $C_1$-$C_4$ alkyl and mixtures thereof, preferably hydrogen. The degree of permanent quaternization of formula (II) may be from 0% to 22% of the polyethyleneimine backbone nitrogen atoms. The molecular weight of this polyethyleneimine preferably is between 10,000 and 15,000.

An alternative polyethyleneimine has the general structure of Formula (II) but wherein the polyethyleneimine backbone has a weight average molecular weight of 600, n of Formula (II) has an average of 24, m of Formula (II) has an average of 16 and R of Formula (II) is selected from hydrogen, a $C_1$-$C_4$ alkyl and mixtures thereof, preferably hydrogen. The degree of permanent quaternization of Formula (II) may be from 0% to 22% of the polyethyleneimine backbone nitrogen atoms. The molecular weight of this polyethyleneimine preferably is between 25,000 and 30,000.

Most preferred polyethyleneimine has the general structure of Formula (II) wherein the polyethyleneimine backbone has a weight average molecular weight of 600, n of Formula (II) has an average of 24, m of Formula (II) has an average of 16 and R of Formula (II) is hydrogen. The degree of permanent quaternization of Formula (II) is 0% of the polyethyleneimine backbone nitrogen atoms. The molecular weight of this polyethyleneimine preferably is from 25,000 to 30,000, most preferably 28,000.

These polyethyleneimines can be prepared, for example, by polymerizing ethyleneimine in the presence of a catalyst such as carbon dioxide, sodium bisulfite, sulfuric acid, hydrogen peroxide, hydrochloric acid, acetic acid, and the like, as described in more detail in PCT Publication No. WO 2007/135645.

Chelant

The detergent composition herein can comprise a chelant at a level of from 0.1% to 20%, preferably from 0.2% to 5%, more preferably from 0.2% to 3% by weight of total composition.

As commonly understood in the detergent field, chelation herein means the binding or complexation of a bi- or multidentate ligand. These ligands, which are often organic compounds, are called chelants, chelators, chelating agents, and/or sequestering agent. Chelating agents form multiple bonds with a single metal ion. Chelants, are chemicals that form soluble, complex molecules with certain metal ions, inactivating the ions so that they cannot normally react with other elements or ions to produce precipitates or scale, or forming encrustations on soils turning them harder to be removed. The ligand forms a chelate complex with the substrate. The term is reserved for complexes in which the metal ion is bound to two or more atoms of the chelant.

Preferably, the composition of the present invention comprises one or more chelant, preferably selected from the group comprising carboxylate chelants, amino carboxylate chelants, amino phosphonate chelants such as MGDA (methylglycine-N,N-diacetic acid), GLDA (glutamic-N,N-diacetic acid), and mixtures thereof.

Suitable chelating agents can be selected from the group consisting of amino carboxylates, amino phosphonates, polycarboxylate chelating agents and mixtures thereof.

Other chelants include homopolymers and copolymers of polycarboxylic acids and their partially or completely neutralized salts, monomeric polycarboxylic acids and hydroxycarboxylic acids and their salts. Suitable polycarboxylic acids are acyclic, alicyclic, heterocyclic and aromatic carboxylic acids, in which case they contain at least two carboxyl groups which are in each case separated from one another by, preferably, no more than two carbon atoms. A suitable hydroxycarboxylic acid is, for example, citric acid. Another suitable polycarboxylic acid is the homopolymer of acrylic acid. Preferred are the polycarboxylates end capped with sulfonates.

Adjunct Ingredients

The cleaning composition herein may optionally comprise a number of other adjunct ingredients such as builders (e.g., preferably citrate), cleaning solvents, cleaning amines, conditioning polymers, cleaning polymers, surface modifying polymers, soil flocculating polymers, structurants, emollients, humectants, skin rejuvenating actives, enzymes, carboxylic acids, scrubbing particles, bleach and bleach activators, perfumes, malodor control agents, pigments, dyes, opacifiers, beads, pearlescent particles, microcapsules, inorganic cations such as alkaline earth metals such as Ca/Mg-ions, antibacterial agents, preservatives, viscosity adjusters (e.g., salt such as NaCl, and other mono-, di- and trivalent salts) and pH adjusters and buffering means (e.g., carboxylic acids such as citric acid, HCl, NaOH, KOH, alkanolamines, phosphoric and sulfonic acids, carbonates such as sodium carbonates, bicarbonates, sesquicarbonates, borates, silicates, phosphates, imidazole and alike).

Method of Washing

In another aspect, the invention is directed to a method of manually washing dishware comprising the steps of delivering a cleaning composition of the invention into a volume of water to form a wash solution and immersing the dishware in the solution. As such, the composition herein will be applied in its diluted form to the dishware. Soiled surfaces e.g. dishes are contacted with an effective amount, typically from 0.5 mL to 20 mL (per 25 dishes being treated), preferably from 3 mL to 10 mL, of the detergent composition of the present invention, preferably in liquid form, diluted in water. The actual amount of detergent composition used will be based on the judgment of user, and will typically depend upon factors such as the particular product formulation of the composition, including the concentration of active ingredients in the composition, the number of soiled dishes to be cleaned, the degree of soiling on the dishes, and the like. Generally, from 0.01 mL to 150 mL, preferably from 3 mL to 40 mL of a liquid detergent composition of the invention is combined with from 2,000 mL to 20,000 mL, more typically from 5,000 mL to 15,000 mL of water in a sink having a volumetric capacity in the range of from 1,000 mL to 20,000 mL, more typically from 5,000 mL to 15,000 mL. The soiled dishes are immersed in the sink containing the diluted compositions then obtained, where contacting the soiled surface of the dish with a cloth, sponge, or similar article cleans them. The cloth, sponge, or similar article may be immersed in the detergent composition and water mixture prior to being contacted with the dish surface, and is typically contacted with the dish surface for a period of time ranged from 1 to 10 seconds, although the actual time will vary with each application and user. The contacting of cloth, sponge, or similar article to the surface is preferably accompanied by a concurrent scrubbing of the surface.

In another aspect, the invention is directed to a method of manually washing dishware with the composition of the present invention. The method comprises the steps of: i) delivering a composition of the present invention onto the dishware or a cleaning implement; ii) cleaning the dishware with the composition in the presence of water; and iii) optionally, rinsing the dishware. The delivering step is preferably either directly onto the dishware surface or onto a cleaning implement, i.e., in a neat form. The cleaning device or implement is preferably wet before or after the composition is delivered to it. Especially good grease removal has been found when the composition is used in neat form.

In another aspect, the invention is directed to a method of manually washing soiled articles preferably dishware comprising contacting a cleaning composition with a surface preferably dishware, wherein the composition comprises one or more BslA proteins, wherein the BslA proteins are a Class III or Class IV BslA Protein as claimed, and wherein the composition modifies the hydrophobicity of the surface preferably dishware as a result of the contacting step.

Another aspect of the present invention is directed to a method of improving suds longevity or grease emulsification in a washing process for washing soiled articles, preferably dishware. The method comprises the steps of: a) delivering a cleaning composition comprising one or more Class III or Class IV BslA proteins as claimed and a specific surfactant system to a volume of water to form a wash liquor; and b) immersing the soiled articles preferably dishware into said wash liquor. Preferably, the BslA proteins are present at a concentration of from 0.005 ppm to 60 ppm, preferably at a concentration of from 0.02 ppm to 12 ppm, based on active protein, in an aqueous wash liquor during the washing process.

In another aspect, the invention is directed use of one or more Class III or Class IV BslA proteins to provide increased suds longevity and/or increase grease emulsification in an aqueous wash liquor during a washing process. Preferably the aqueous wash liquor further comprises a surfactant system comprising one or more anionic surfactants and one or more co-surfactants selected from the group consisting of amphoteric surfactant, zwitterionic surfactant, and mixtures thereof.

TEST METHODS

The following assays set forth must be used in order that the invention described and claimed herein may be more fully understood.

Test Method 1—Glass Vial Suds Mileage Method

The objective of the glass vial suds mileage test method is to measure the evolution of suds volume over time generated by a certain solution of detergent composition in the presence of a greasy soil, e.g., olive oil. The steps of the method are as follows:
1. Test solutions are prepared by subsequently adding aliquots at room temperature of: a) 10 g of an aqueous detergent solution at specified detergent concentration and water hardness, b) 1.0 g of an aqueous protein solution at specified concentration and water hardness, and c) 0.11 g of olive oil (Bertolli®, Extra Virgin Olive Oil), into a 40 mL glass vial (dimensions: 95 mm H×27.5 mm D). For the reference samples, the protein solutions are substituted with 1.0 mL of demineralized water. For the nil detergent samples, the 10 g of aqueous detergent solution is replaced by 10 g of water at specified water hardness.
2. The test solutions are mixed in the closed test vials by stirring at room temperature for 2 minutes on a magnetic stirring plate (IKA, model # RTC B 5001; VWR magnetic stirrer, catalog #58949-012; 500 RPM), followed by manually shaking for 20 seconds with an upwards downwards movement (about 2 up and down cycles per second, +/−30 cm up and 30 cm down).
3. Following the shaking, the test solutions in the closed vials are further stirred on a magnetic stirring plate (IKA, model # RTC B 5001; VWR magnetic stirrer, catalog #58949-012; 500 RPM) for 60 minutes inside a water bath at 46° C. to maintain a constant temperature. The samples are then shaken manually for another 20 seconds as described above and the initial suds heights (H1) are recorded with a ruler.
4. The samples are incubated for an additional 30 minutes inside the water bath at 46° C. while stirring (IKA, model # RTC B 5001; VWR magnetic stirrer, catalog #58949-012; 500 RPM), followed by manual shaking for another 20 seconds as described above. The final suds heights (H2) are recorded.
5. Protein solutions that produce larger suds heights (H1 and H2), preferably combined with lower drops in suds height between H1 and H2, are more desirable.

Test Method 2—Sink Suds Mileage Method

The evolution of the suds volume generated by a solution of a detergent composition can be determined while adding soil loads periodically as follows. A stream of hard water (15 dH) fills a sink (cylinder dimensions: 300 mm D×288 mm H) to 4 L with a constant pressure of 4 bar. Simultaneously, an aliquot of the detergent composition (final concentration 0.12 w %) is dispensed through a pipette with a flow rate of 0.67 mL/sec at a height of 37 cm above the bottom of the sink surface. An initial suds volume is generated in the sink due to the pressure of the water. The temperature of the solution is maintained at 46° C. during the test.

After recording the initial suds volume (average suds height×sink surface area), a fixed amount of greasy soil (Composition: see Table 1, 6 mL) is injected in the middle of the sink, while a paddle (dimensions: 10 cm×5 cm, positioned in the middle of the sink at the air liquid interface at an angle of 45 degrees) rotates 20 times into the solution at 85 RPM. This step is followed immediately by another measurement of the total suds volume. The soil injecting, paddling, and measuring steps are repeated until the measured suds volume reaches a minimum level, which is set at 400 cm$^3$. The amount of soil additions needed to get to that level is recorded. The complete process is repeated a number of times and the average of the number of additions for all the replicates is calculated for each detergent composition Finally, the suds mileage index is then calculated as: (average number of soil additions for test detergent composition)/(average number of soil additions for reference detergent composition)×100.

Pending on the test purpose the skilled person could choose to select an alternative water hardness, solution temperature, product concentration or soil type.

TABLE 1

| Greasy Soil Composition | |
| --- | --- |
| Ingredient | Weight % |
| Crisco oil | 12.730 |
| Crisco shortening | 27.752 |
| Lard | 7.638 |
| Refined Rendered Edible Beef Tallow | 51.684 |
| Oleic Acid, 90% (Techn) | 0.139 |
| Palmitic Acid, 99+% | 0.036 |
| Stearic Acid, 99+% | 0.021 |

EXAMPLES

The following examples are provided to further illustrate the present invention and are not to be construed as limitations of the present invention, as many variations of the present invention are possible without departing from its spirit or scope.

Example 1a—Production of *Thermoactinomyces vulgaris* BslA_Class III

A codon optimized gene (SEQ ID NO: 25) encoding for a *Thermoactinomyces vulgaris* BslA_ClassIII variant, without the N-terminal signal peptide but including an N-terminal His-tag and a TEV protease cleavage site (SEQ ID NO: 26), is designed and synthesized. After gene synthesis, the protein is expressed and purified by Genscript (Piscataway, N.J.). In brief, the complete synthetic gene sequence is subcloned into a pET30a vector for heterologous expression. *Escherichia coli* BL21 (DE3) cells are transformed with the recombinant plasmid and a single colony is inoculated into TB medium containing kanamycin. Isopropyl β-D-1-thiogalactopyranoside (IPTG) is added (final concentration 0.1 mM) to induce protein expression and the culture is incubated at 37° C. for 4 hrs. Cells are harvested by centrifugation and the pellets are lysed by sonication. After centrifugation, the supernatant is collected and the protein is purified by one-step purification using a nickel affinity column and standard protocols known in the art. The protein is stored in a buffer containing 50 mM Tris-HCl, 150 mM NaCl, and 10% Glycerol at pH 8.0. The final protein concentration is 0.193 mg/mL as determined by Bradford protein assay with BSA as a standard (ThermoFisher, catalog #23236).

Example 1b—Production of *Bacillus licheniformis* BslA_Class IV

A codon optimized gene (SEQ ID NO: 27) encoding for a *Bacillus licheniformis* BslA_ClassIV variant, without the N-terminal signal peptide but including an N-terminal His-tag and a TEV protease cleavage site (SEQ ID NO: 28), is designed and synthesized. After gene synthesis, the protein is expressed and purified by Genscript (Piscataway, N.J.). In brief, the complete synthetic gene sequence is subcloned into a pET30a vector for heterologous expression. *Escherichia coli* BL21 Star (DE3) cells are transformed with the recombinant plasmid and a single colony was inoculated into TB medium containing kanamycin. When $OD_{600}$ reached 4, isopropyl β-D-1-thiogalactopyranoside (IPTG) is added (final concentration 0.1 mM) to induce protein expression and the culture is incubated at 15° C. for 16 h. Cells are harvested by centrifugation and the pellets are lysed by sonication. After centrifugation, the pellet is dissolved using urea and the protein is purified by one-step purification using a nickel affinity column and standard protocols known in the art. The protein is refolded and stored in buffer containing 1×PBS and 0.5% Sodium Lauroyl Sarcosine at pH 7.4. The final protein concentration is 0.60 mg/mL as determined by Bradford protein assay with BSA as a standard (ThermoFisher, catalog #23236).

Example 1c—Production of *Bacillus subtilis* YuaB_classIa

A codon optimized gene (SEQ ID NO: 29) encoding for a *Bacillus subtilis* YuaB_classIa variant, without the N-terminal signal peptide but including an N-terminal His-tag and a TEV protease cleavage site (SEQ ID NO: 30), is designed and synthesized. After gene synthesis, the protein is expressed and purified by Genscript (Piscataway, N.J.). In brief, the complete synthetic gene sequence is subcloned into a pET30a vector for heterologous expression. *Escherichia coli* BL21 (DE3) cells are transformed with the recombinant plasmid and a single colony is inoculated into TB medium containing the proper kanamycin. Isopropyl β-D-1-thiogalactopyranoside (IPTG) is added (final concentration 0.1 mM) to induce protein expression and the culture is incubated at 37° C. for 4 hrs. Cells are harvested by centrifugation and the pellets are lysed by sonication. After centrifugation, the supernatant was collected and the protein is purified by one-step purification using a nickel affinity column and standard protocols known in the art. The protein is stored in a buffer containing 50 mM Tris-HCl, 150 mM NaCl, and 10% Glycerol at pH 8.0. The final protein concentration is 6.10 mg/mL as determined by Bradford protein assay with BSA as a standard (ThermoFisher, catalog #23236).

Example 1d—Production of *Bacillus velezensis* YweA_classII

A codon optimized gene (SEQ ID NO: 31) encoding for a *Bacillus velezensis* YweA_classII variant, without the N-terminal signal peptide but including an N-terminal His-tag and a TEV protease cleavage site (SEQ ID NO: 32), is designed and synthesized. After gene synthesis, the protein is expressed and purified by Genscript (Piscataway, N.J.). In brief, the complete synthetic gene sequence is subcloned into a pET30a vector for heterologous expression. *Escherichia coli* BL21 (DE3) cells are transformed with the recombinant plasmid and a single colony is inoculated into TB medium containing the proper kanamycin. Isopropyl β-D-1-thiogalactopyranoside (IPTG) is added (final concentration 0.1 mM) to induce protein expression and the culture is incubated at 37° C. for 4 h. Cells are harvested by centrifugation and the pellets are lysed by sonication. After centrifugation, the supernatant is collected and the protein is purified by one-step purification using a nickel affinity column and standard protocols known in the art. The protein is stored in a buffer containing 50 mM Tris-HCl, 150 mM NaCl, and 10% Glycerol at pH 8.0. The final protein concentration is 4.50 mg/mL as determined by Bradford protein assay with BSA as a standard (ThermoFisher, catalog #23236).

Example 1e—Detergent Compositions

The evolution of suds volume generated by a certain solution of detergent composition in presence of a soil, i.e., olive oil or greasy soil, is followed over time under specific conditions (e.g., water hardness, solution temperature, detergent concentrations, etc.). The following solutions are prepared:

A. Hard water (15 dH): 0.75 g $MgCl_2.6H_2O$ (Sigma-Aldrich, catalog # M9272), 2.10 g $CaCl_2.6H_2O$ (Sigma-Aldrich, catalog #21108), and 0.689 g $NaHCO_3$ (Sigma-Aldrich, catalog #31437) are dissolved in 5 L of demineralized water.
B. Detergent solution of a high surfactant content detergent composition ("solution DG-HS") is prepared using Fairy Dark Green, as commercially available in the UK in February 2017, diluted in hard water (15 dH) prepared as above, at targeted detergent concentration of 0.12%.
C. Detergent solution of a low surfactant content detergent composition ("solution DG-LS") is prepared using Fairy Dark Green, as commercially available in the UK in February 2017, diluted in hard water (15 dH) prepared as above, at targeted detergent concentration of 0.06%.
D. Protein solutions: Proteins are diluted in demineralized water to the required concentration before proceeding with the suds mileage method.
E. Greasy soil: A grease soil is prepared according to the composition described in Table 1.

Example 2—Glass Vial Suds Mileage of *Thermoactinomyces vulgaris* BslA_ClassIII with Olive Oil Inventive Compositions A and B are examples of cleaning compositions according to the present invention, made with: a) detergent solution DG-LS comprising a surfactant system according to the invention (prepared as described in Example 1e), and b) diluted samples of purified *Thermoactinomyces vulgaris* BslA_ClassIII (SEQ ID NO: 26) (prepared as described in Example 1a) proteins according to the invention. Comparative Composition C contains the same detergent solution DG-LS comprising a surfactant system according to the invention but in the absence of the BslA protein according to the invention. The glass vial suds mileage test is performed on the compositions using olive oil as described in the test methods section (Test Method 1). The initial (H1) and final (H2) measurements are recorded in Table 2. The % suds height drop represents the drop in suds height as measured between the initial and final time point and is calculated by the following equation:

$$\% \text{ suds height drop} = \{(H1-H2)/H1\}*100\%.$$

The % suds height drops are calculated for the compositions and shown in Table 2.

TABLE 2

Suds Mileage

| Composition | BslA Class III Concentration in the Composition [ppm] | H1 [mm] | H2 [mm] | % suds height drop H2 vs H1 |
|---|---|---|---|---|
| Inventive Composition A | 60 | 10 | 10 | 0% |
| Inventive Composition B | 12 | 9.5 | 6 | 37% |
| Comparative Composition C | 0 | 5 | 3 | 40% |

The results confirm that Inventive Compositions A and B detergent solutions comprising a surfactant system and *Thermoactinomyces vulgaris* BslA_Class III (SEQ ID NO: 26) according to the invention have a superior suds profile compared to Comparative Composition C solution comprising the surfactant composition according to the invention but without the BslA protein according to the invention, both in view of absolute suds height build-up as in view of sustaining the suds height in presence of greasy soil.

Example 3—Glass Vial Suds Mileage of *Bacillus licheniformis* BslA_ClassIV with Olive Oil Inventive Compositions D and E are examples of cleaning compositions according to the present invention, made with: a) detergent solution DG-LS (prepared as described in Example 1e) comprising a surfactant composition according to the invention, and b) diluted samples of purified *Bacillus licheniformis* BslA_Class IV (SEQ ID NO: 28) (prepared as described in Example 1b) proteins according to the invention. Comparative Composition F contains the same detergent solution DG-LS comprising the surfactant composition according to the invention but in the absence of the BslA protein according to the invention. The glass vial suds mileage test is performed on the compositions using olive oil as described in the test methods section (Test Method 1). The initial (H1) and final (H2) measurements are recorded in Table 2. The % suds height drops are calculated for the compositions and shown in Table 3.

TABLE 3

Suds Mileage

| Composition | BslA Class IV Concentration in the Composition [ppm] | H1 [mm] | H2 [mm] |
|---|---|---|---|
| Inventive Composition D | 55 | 11 | 10 |

TABLE 3-continued

Suds Mileage

| Composition | BslA Class IV Concentration in the Composition [ppm] | H1 [mm] | H2 [mm] |
|---|---|---|---|
| Inventive Composition E | 12 | 5 | 0.5 |
| Comparative Composition F | 0 | 1 | 0 |

The results confirm that Inventive Compositions D and E detergent solutions comprising a surfactant system and *Bacillus licheniformis* BslA_Class IV (SEQ ID NO: 28) according to the invention have a superior suds profile compared to Comparative Composition F solution comprising a surfactant system according to the invention but without the BslA protein according to the invention, especially in view of absolute suds height build-up.

Example 4—Comparison of Glass Vial Suds Mileage of *Thermoactinomyces vulgaris* BslA_Class III and Other BslA Proteins Inventive Composition J is an example of a cleaning composition according to the present invention, made with: a) detergent solution DG-LS (prepared as described in Example 1e) comprising a surfactant system according to the invention, and b) diluted sample of purified *Thermoactinomyces vulgaris* BslA_Class III (SEQ ID NO: 26) (prepared as described in Example 1a) protein according to the invention.

Comparative Compositions H and I are examples of cleaning composition outside the scope of the present invention, made with a) detergent solution DG-LS (prepared as described in Example 1e) comprising a surfactant system according to the invention, and b) diluted samples of purified *Bacillus subtilis* YuaB_Class Ia (SEQ ID NO: 30), or *Bacillus velezensis* YweA_Class II (SEQ ID NO: 32) (prepared as described in Example 1c and 1e), respectively, proteins outside the scope of the invention. Comparative Composition G contains the same detergent solution DG-LS in the absence of the *Bacillus subtilis* YuaB_Class Ia (SEQ ID NO: 30), or *Bacillus velezensis* YweA_Class II (SEQ ID NO: 32) proteins.

Comparative Compositions K, L, and M are also examples of cleaning composition outside the scope of the present invention, made with diluted samples of purified *Bacillus subtilis* YuaB_Class Ia (SEQ ID NO: 30), *Bacillus velezensis* YweA_Class II (SEQ ID NO: 32), or *Thermoactinomyces vulgaris* BslA_Class III (SEQ ID NO: 26), respectively, in the absence of the detergent solution DG-LS (replaced with hard water—15 dH).

The glass vial suds mileage test is performed on the compositions using olive oil as described in the test methods section (Test Method 1). The initial (H1) and final (H2) measurements are recorded in Table 4. The % suds height drops are calculated for the compositions and shown in Table 4.

TABLE 4

Suds Mileage

| Composition | BslA_Protein | Protein Conc. in Composition [ppm] | H1 [mm] | H2 [mm] | % suds height drop H2 vs H1 |
|---|---|---|---|---|---|
| Comparative Composition G | None | 0 | 4.5 | 3 | 33% |

TABLE 4-continued

Suds Mileage

| Composition | BslA_Protein | Protein Conc. in Composition [ppm] | H1 [mm] | H2 [mm] | % suds height drop H2 vs H1 |
|---|---|---|---|---|---|
| Comparative Composition H | Bacillus subtilis YuaB_Class Ia (SEQ ID NO: 30) | 60 | 5.5 | 5 | 9% |
| Comparative Composition I | Bacillus velezensis YweA_Class II (SEQ ID NO: 32) | 60 | 7 | 4.5 | 36% |
| Inventive Composition J | Thermoactinomyces vulgaris BslA Class III (SEQ ID NO: 26) | 60 | 10 | 10 | 0% |
| Comparative Composition K | Bacillus subtilis YuaB_Class Ia (SEQ ID NO: 30) | 60 | 0 | 0 | not applicable (no suds) |
| Comparative Composition L | Bacillus velezensis YweA_Class II (SEQ ID NO: 32) | 60 | 0 | 0 | not applicable (no suds) |
| Comparative Composition M | Thermoactinomyces vulgaris BslA Class III (SEQ ID NO: 26) | 60 | 0 | 0 | not applicable (no suds) |

The results confirm that Inventive Composition J detergent solution comprising a surfactant system and *Thermoactinomyces vulgaris* BslA_Class III (SEQ ID NO: 26) protein according to the invention have a superior suds profile compared to Comparative Compositions H and I solutions comprising a surfactant system according to the invention but Class I and II BslA proteins outside the scope of the invention under the tested conditions, both in view of absolute suds height build-up as in view of sustaining the suds height in presence of greasy soil. Comparative Compositions K, L and M comprising various BslA proteins without the specific surfactant system produced no suds. The absence of suds formation in Comparative Composition M comprising a protein according to the invention but lacking a surfactant system according to the invention illustrates the synergistic suds boost between the specific surfactant system and specific protein according to the invention.

Example 5—Comparison of Glass Vial Suds Mileage of *Bacillus licheniformis* BslA_Class IV and Other BslA Proteins Inventive Composition Q is an example of a cleaning composition according to the present invention, made with a) detergent solution DG-LS comprising a surfactant system according to the invention, and b) diluted sample of purified *Bacillus licheniformis* BslA_Class IV (SEQ ID NO: 28) (prepared as described in Example 1b) protein according to the invention.

Comparative Compositions O and P are examples of cleaning composition outside the scope of the present invention, made with a) detergent solution DG-LS (prepared as described in Example 1e) comprising a surfactant system according to the invention, and b) diluted samples of purified *Bacillus subtilis* YuaB_Class Ia (SEQ ID NO: 30), or *Bacillus velezensis* YweA_Class II (SEQ ID NO: 32) (prepared as described in Example 1c and 1e), respectively, proteins outside the scope of the invention. Comparative Composition N contains the same detergent solution DG-LS comprising the surfactant system according to the invention but in the absence of the *Bacillus subtilis* YuaB_Class Ia (SEQ ID NO: 30), or *Bacillus velezensis* YweA_Class II (SEQ ID NO: 32) proteins.

Comparative Compositions R, S, and T are also examples of cleaning composition outside the scope of the present invention, made with diluted samples of purified *Bacillus subtilis* YuaB_Class Ia (SEQ ID NO: 30), *Bacillus velezensis* YweA_Class II (SEQ ID NO: 32), or *Bacillus licheniformis* BslA_Class IV (SEQ ID NO: 28), respectively, in the absence of the detergent solution DG-LS (replaced with hard water—15 dH).

The glass vial suds mileage test is performed on the compositions using olive oil as described in the test methods section (Test Method 1). The initial (H1) and final (H2) measurements are recorded in Table 5.

TABLE 5

Suds Mileage

| Composition | BslA_Protein | Protein Conc. in Composition [ppm] | H1 [mm] | H2 [mm] |
|---|---|---|---|---|
| Comparative Composition N | None | 0 | 5 | 4 |
| Comparative Composition O | Bacillus subtilis YuaB_Class Ia (SEQ ID NO: 30) | 48 | 8 | 8 |
| Comparative Composition P | Bacillus velezensis YweA_Class II (SEQ ID NO: 32) | 48 | 8 | 8 |
| Inventive Composition Q | Bacillus licheniformis BslA_Class IV (SEQ ID NO: 28) | 48 | 32 | 24 |
| Comparative Composition R | Bacillus subtilis YuaB_Class Ia (SEQ ID NO: 30) | 48 | 0 | 0 |
| Comparative Composition S | Bacillus velezensis YweA_Class II (SEQ ID NO: 32) | 48 | 0 | 0 |
| Comparative Composition T | Bacillus licheniformis BslA_Class IV (SEQ ID NO: 28) | 48 | 0 | 0 |

The results confirm that Inventive Composition Q detergent solution comprising a surfactant system and *Bacillus licheniformis* BslA Class IV (SEQ ID NO: 28) according to the invention has a superior suds profile compared to Comparative Compositions 0 and P solutions comprising a surfactant system according to the invention but Class I and II BslA proteins outside the scope of the invention under the tested conditions, especially in view of absolute suds height build-up. Comparative Compositions R, S and T comprising various BslA proteins without the specific surfactant system produced no suds. The absence of suds formation in Comparative Composition T comprising a protein according to the invention but lacking a surfactant system according to the invention illustrates the synergistic suds boost between the specific surfactant system and specific protein according to the invention.

Example 6—Exemplary Manual Dish-Washing Detergent Composition

Table 6 exemplifies a manual dish-washing detergent composition comprising *Thermoactinomyces vulgaris* BslA_Class III (SEQ ID NO: 6) protein according to the invention.

TABLE 6

Detergent Composition

| Ingredient | Wt % |
| --- | --- |
| Sodium alkyl ethoxy sulfate (C1213EO0.6S) | 22.91% |
| n-C12-14 Di Methyl Amine Oxide | 7.64% |
| Lutensol ® XP80 (non-ionic surfactant supplied by BASF) | 0.45% |
| Sodium Chloride | 1.2% |
| Poly Propylene Glycol (MW 2000) | 1% |
| Ethanol | 2% |
| Sodium Hydroxide | 0.24% |
| *Thermoactinomyces vulgaris* BslA_Class III (SEQ ID NO: 6) | 0.5% |
| Minors (perfume, preservative, dye) + water | To 100% |
| pH (@ 10% solution) | 9 |

All percentages and ratios given for proteins are based on active protein. All percentages and ratios herein are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A cleaning composition comprising one or more BslA (Biofilm surface layer A) proteins and a surfactant system comprising one or more anionic surfactants and one or more co-surfactants, wherein the weight ratio of the anionic surfactants to the co-surfactants is less than about 9:1, wherein the BslA proteins are a Class III or a Class IV BslA protein, wherein the Class III BslA protein has at least 80% amino acid identity as calculated over the entire length of a sequence aligned against the entire length of a wild-type protein sequence: *Thermoactinomyces vulgaris* BslA (SEQ ID NO: 6), and wherein the Class IV BslA protein has at least 80% amino acid identity as calculated over the entire length of a sequence aligned against the entire length of a wild-type protein sequence selected from the group consisting of: *Bacillus licheniformis* BslA (SEQ ID NO: 7, SEQ ID NO: 8, SEQ ID NO: 9, SEQ ID NO: 10, and SEQ ID NO: 11), *B. glycinifermentans* BslA (SEQ ID NO: 12, SEQ ID NO: 13, SEQ ID NO: 14, and SEQ ID NO: 15), *B. sonorensis* BslA (SEQ ID NO: 16), *B. paralicheniformis* BslA (SEQ ID NO: 17, and SEQ ID NO: 18), and *Bacillus* sp. BslA (SEQ ID NO: 19, SEQ ID NO: 20, SEQ ID NO: 21, and SEQ ID NO: 22).

2. The composition according to claim 1 wherein the Class III BslA protein has at least 85% amino acid identity as calculated over the entire length of a sequence aligned against the entire length of a wild-type protein sequence: *Thermoactinomyces vulgaris* BslA (SEQ ID NO: 6), and the Class IV BslA protein has at least 85% amino acid identity as calculated over the entire length of a sequence aligned against the entire length of a wild-type protein sequence selected from the group consisting of: sequence selected from the group consisting of: *Bacillus licheniformis* BslA (SEQ ID NO: 7, SEQ ID NO: 8, SEQ ID NO: 9, SEQ ID NO: 10, and SEQ ID NO: 11), *B. glycinifermentans* BslA (SEQ ID NO: 12, SEQ ID NO: 13, SEQ ID NO: 14, and SEQ ID NO: 15), *B. sonorensis* BslA (SEQ ID NO: 16), *B. paralicheniformis* BslA (SEQ ID NO: 17, and SEQ ID NO: 18), and *Bacillus* sp. BslA (SEQ ID NO: 19, SEQ ID NO: 20, SEQ ID NO: 21, and SEQ ID NO: 22).

3. The composition according to claim 1 wherein the Class III BslA protein has at least 90% amino acid identity as calculated over the entire length of a sequence aligned against the entire length of a wild-type protein sequence: *Thermoactinomyces vulgaris* BslA (SEQ ID NO: 6), and the Class IV BslA protein has at least 90% amino acid identity as calculated over the entire length of a sequence aligned against the entire length of *B. licheniformis* BslA (SEQ ID NO: 7).

4. The composition according to claim 1, wherein the BslA proteins are present in an amount of from about 0.01 wt % to about 5 wt %, by weight of the cleaning composition, based on active protein.

5. The composition according to claim 1, wherein the surfactant system is present in an amount of from about 1 wt % to about 60 wt % by weight of the cleaning composition.

6. The composition according to claim 1, further comprising one or more carbohydrates selected from the group comprising O-glycan, N-glycan, and mixtures thereof.

7. The composition according to claim 1, wherein the weight ratio of the anionic surfactants to the co-surfactants is from about 5:1 to about 1:1.

8. The composition according to claim 1, wherein the anionic surfactants are selected from the group consisting of: alkyl sulfates, alkyl alkoxy sulfates, alkyl benzene sulfonates, paraffin sulfonates, and mixtures thereof.

9. The composition according to claim 1, wherein the co-surfactants are selected from the group consisting of amphoteric surfactant, zwitterionic surfactant, and mixtures thereof.

10. The composition according to claim 9, wherein the amphoteric surfactant is amine oxide surfactant and the zwitterionic surfactant is betaine surfactant.

11. The composition according to claim 1, wherein the anionic surfactants are a mixture of alkyl sulfates and alkyl alkoxy sulfates, the co-surfactants are alkyl dimethyl amine oxides, and wherein the weight ratio of the anionic surfactants to the co-surfactants is from 4:1 to 2:1.

12. The composition according to claim 1, further comprising one or more non-ionic surfactants.

13. The composition according to claim 1, wherein the composition is a manual dishwashing composition.

14. The composition according to claim 1, further comprising a chelant selected from the group comprising carboxylate chelants, amino carboxylate chelants, amino phosphonate chelants, and mixtures thereof.

15. The composition according to claim 14, wherein the chelant is selected from the group consisting of MGDA (methylglycine-N,N-diacetic acid), GLDA (glutamic-N,N-diacetic acid), and mixtures thereof.

16. The composition according to claim 1, further comprising one or more enzymes selected from the group consisting of amylases, lipases, proteases, cellulases, lipoxygenases, diol synthases, and mixtures thereof.

17. A method of improving suds longevity and/or grease emulsification in a washing process for washing soiled articles comprising the steps of:
   a) delivering a cleaning composition according to claim 1 to a volume of water to form a wash liquor; and
   b) immersing the soiled articles into the wash liquor.

18. The method of claim 17, wherein the BslA proteins are present at a concentration of from about 0.005 ppm to about 60 ppm, based on active protein, in an aqueous wash liquor during the washing process.

* * * * *

SEQUENCE LISTING

<160> NUMBER OF SEQ ID NOS: 32

<210> SEQ ID NO 1
<211> LENGTH: 181
<212> TYPE: PRT
<213> ORGANISM: Bacillus subtilis

<400> SEQUENCE: 1

```
Met Lys Arg Lys Leu Leu Ser Ser Leu Ala Ile Ser Ala Leu Ser Leu
1               5                   10                  15

Gly Leu Leu Val Ser Ala Pro Thr Ala Ser Phe Ala Ala Glu Ser Thr
            20                  25                  30

Ser Thr Lys Ala His Thr Glu Ser Thr Met Arg Thr Gln Ser Thr Ala
        35                  40                  45

Ser Leu Phe Ala Thr Ile Thr Gly Ala Ser Lys Thr Glu Trp Ser Phe
    50                  55                  60

Ser Asp Ile Glu Leu Thr Tyr Arg Pro Asn Thr Leu Leu Ser Leu Gly
65                  70                  75                  80

Val Met Glu Phe Thr Leu Pro Ser Gly Phe Thr Ala Asn Thr Lys Asp
                85                  90                  95
```

```
Thr Leu Asn Gly Asn Ala Leu Arg Thr Thr Gln Ile Leu Asn Asn Gly
            100                 105                 110

Lys Thr Val Arg Val Pro Leu Ala Leu Asp Leu Leu Gly Ala Gly Glu
        115                 120                 125

Phe Lys Leu Lys Leu Asn Asn Lys Thr Leu Pro Ala Ala Gly Thr Tyr
    130                 135                 140

Thr Phe Arg Ala Glu Asn Lys Ser Leu Ser Ile Gly Asn Lys Phe Tyr
145                 150                 155                 160

Ala Glu Ala Ser Ile Asp Val Ala Lys Arg Ser Thr Pro Pro Thr Gln
                165                 170                 175

Pro Cys Gly Cys Asn
            180

<210> SEQ ID NO 2
<211> LENGTH: 181
<212> TYPE: PRT
<213> ORGANISM: Bacillus amyloliquefaciens

<400> SEQUENCE: 2

Met Lys Met Lys His Lys Phe Phe Ser Thr Val Met Ala Ser Leu Phe
1               5                   10                  15

Gly Leu Val Leu Leu Ser Leu Pro Thr Ala Ser Phe Ala Ala Glu
            20                  25                  30

Ser Ser Ser Thr Val His Glu Pro Glu Met Ser Thr Lys Ala Thr Ala
        35                  40                  45

Thr Leu Phe Ala Lys Tyr Thr Gly Ala Ser Gln Gln Glu Trp Ser Phe
    50                  55                  60

Ser Asp Ile Glu Leu Thr Tyr Arg Pro Asn Thr Ile Leu Ser Leu Gly
65                  70                  75                  80

Val Met Glu Phe Thr Leu Pro Ser Gly Phe Ala Thr Thr Lys Asp
                85                  90                  95

Thr Val Asn Gly His Ala Leu Arg Glu Arg Gln Ile Leu Asn Asn Gly
            100                 105                 110

Lys Thr Val Arg Leu Pro Leu Asn Ile Asp Leu Ile Gly Ala Ala Glu
        115                 120                 125

Phe Lys Leu Ser Leu Asn Asn Lys Thr Leu Pro Ala Ala Gly Thr Tyr
    130                 135                 140

Lys Phe Arg Ala Glu Asn Lys Ser Leu Ser Ile Gly Ser Lys Phe Tyr
145                 150                 155                 160

Ala Glu Asp Thr Ile Val Val Gln Lys Arg Ser Thr Pro Pro Thr Gln
                165                 170                 175

Pro Cys Asn Cys Lys
            180

<210> SEQ ID NO 3
<211> LENGTH: 179
<212> TYPE: PRT
<213> ORGANISM: Bacillus licheniformis

<400> SEQUENCE: 3

Met Lys Arg Met Tyr Arg Ser Lys Leu Ser Ile Leu Ala Val Ser Leu
1               5                   10                  15

Val Met Met Ala Ser Ile Phe Leu Pro Ser Phe Gln Ala Ser Ala Gln
            20                  25                  30

Thr Thr Lys Thr Glu Ser Val Tyr Arg Pro Ala Ala Ser Ala Ser Leu
        35                  40                  45
```

```
Tyr Ser Val Ile Thr Gly Ala Ser Lys Gln Glu Trp Ser Phe Ser Asp
            50                  55                  60

Ile Glu Leu Thr Tyr Arg Pro Asn Ser Ile Leu Ala Leu Gly Thr Val
65                  70                  75                  80

Glu Phe Thr Leu Pro Ser Gly Phe Ser Ala Thr Thr Lys Asp Thr Val
                85                  90                  95

Asn Gly Arg Ala Leu Thr Thr Gly Gln Ile Leu Asn Asn Gly Lys Thr
            100                 105                 110

Val Arg Leu Pro Leu Thr Ile Asp Leu Leu Gly Ile Ala Glu Phe Lys
                115                 120                 125

Leu Val Leu Ala Asn Lys Thr Leu Pro Ala Ala Gly Lys Tyr Thr Phe
130                 135                 140

Arg Ala Glu Asn Arg Val Leu Gly Leu Gly Ser Thr Phe Tyr Ala Glu
145                 150                 155                 160

Ser Ser Ile Glu Val Gln Lys Arg Ala Thr Pro Pro Thr Gln Pro Cys
                165                 170                 175

Asn Cys Lys
```

<210> SEQ ID NO 4
<211> LENGTH: 177
<212> TYPE: PRT
<213> ORGANISM: Bacillus pumilus

<400> SEQUENCE: 4

```
Met Lys Lys Thr Trp Thr Met Ile Met Met Gly Met Leu Thr Leu Val
1               5                   10                  15

Met Ala Leu Ser Val Pro Ile Ala Ala Ser Ala Glu Gly Ala Thr Gln
                20                  25                  30

Glu Gly Lys Ala Ser Thr Asn Ala Arg Pro Ala Glu Leu Tyr Ala Lys
            35                  40                  45

Ile Thr Gly Thr Ser Lys Gln Glu Trp Ser Phe Ser Asp Ile Glu Leu
        50                  55                  60

Thr Tyr Arg Pro Asn Ser Val Leu Ser Leu Gly Ala Ile Glu Phe Thr
65                  70                  75                  80

Leu Pro Ala Gly Phe Gln Ala Thr Thr Lys Asp Ile Phe Asn Gly Lys
                85                  90                  95

Ala Leu Lys Asp Ser Tyr Ile Leu Asn Ser Gly Lys Thr Val Arg Ile
            100                 105                 110

Pro Ala Arg Leu Asp Leu Leu Gly Ile Ser Gln Phe Lys Leu Gln Leu
        115                 120                 125

Ser His Lys Val Leu Pro Ala Ala Gly Thr Tyr Thr Phe Arg Ala Glu
130                 135                 140

Asn Arg Ala Leu Ser Ile Gly Ser Lys Phe Tyr Ala Glu Asp Thr Leu
145                 150                 155                 160

Asp Ile Gln Thr Arg Pro Val Val Val Thr Pro Pro Asp Pro Cys Gly
                165                 170                 175

Cys
```

<210> SEQ ID NO 5
<211> LENGTH: 154
<212> TYPE: PRT
<213> ORGANISM: Bacillus subtilis

<400> SEQUENCE: 5

```
Met Leu Lys Arg Thr Ser Phe Val Ser Ser Leu Phe Ile Ser Ser Ala
1               5                   10                  15
```

Val Leu Leu Ser Ile Leu Pro Ser Gly Gln Ala His Ala Gln Ser
            20              25              30

Ala Ser Ile Glu Ala Lys Thr Val Asn Ser Thr Lys Glu Trp Thr Ile
        35              40              45

Ser Asp Ile Glu Val Thr Tyr Lys Pro Asn Ala Val Leu Ser Leu Gly
    50              55              60

Ala Val Glu Phe Gln Phe Pro Asp Gly Phe His Ala Thr Thr Arg Asp
65              70              75              80

Ser Val Asn Gly Arg Thr Leu Lys Glu Thr Gln Ile Leu Asn Asp Gly
            85              90              95

Lys Thr Val Arg Leu Pro Leu Thr Leu Asp Leu Gly Ala Ser Glu
            100             105             110

Phe Asp Leu Val Met Val Arg Lys Thr Leu Pro Arg Ala Gly Thr Tyr
        115             120             125

Thr Ile Lys Gly Asp Val Val Asn Gly Leu Gly Ile Gly Ser Phe Tyr
    130             135             140

Ala Glu Thr Gln Leu Val Ile Asp Pro Arg
145             150

<210> SEQ ID NO 6
<211> LENGTH: 163
<212> TYPE: PRT
<213> ORGANISM: Thermoactinomyces vulgaris

<400> SEQUENCE: 6

Met Arg Leu Arg Met Val Trp Leu Ser Val Ile Val Gly Leu Ser Trp
1               5               10              15

Met Leu Val Gly Trp Thr Asn Pro Pro Ala Pro Ala Asp Ala Glu Val
            20              25              30

Pro Ser Lys Trp Gln Ala Ala Gln Gly Lys Ala Leu Thr Val Arg Leu
        35              40              45

Glu Pro Ser Lys Asn Lys Gln Glu Ala Val Ser Asp Val Val Ile Thr
    50              55              60

Tyr Lys Pro Asp Val Val Leu Ala Tyr Gly Arg Ala Lys Phe His Leu
65              70              75              80

Pro Lys Gly Phe Ser Ala Val Ala Gly Asp Leu Ile Asn Gly Gln Pro
            85              90              95

Leu Thr Ala Asp Tyr Ile Gln Asn Gly Gly Gln Thr Val Thr Leu Pro
            100             105             110

Phe Gly Val Asp Ile Gly Ala Met Arg Ile Phe Glu Leu Arg Leu Val
        115             120             125

Gly Lys Lys Leu Pro Ser Ala Gly Gln Tyr Lys Phe Arg Ala Glu Tyr
    130             135             140

Trp Gly Ile Gly Ile Gly Ile Tyr Asn Thr Ala Glu Ala Val Leu Glu
145             150             155             160

Leu Arg Asn

<210> SEQ ID NO 7
<211> LENGTH: 157
<212> TYPE: PRT
<213> ORGANISM: Bacillus licheniformis

<400> SEQUENCE: 7

Met Leu Lys Arg Lys Phe Ile Gly Lys Ile Gly Val Gly Leu Leu Thr
1               5               10              15

```
Ser Ala Ala Leu Phe Ser Phe Ile Leu Pro Thr Glu Glu Ala Ser Ala
            20                  25                  30

Thr Phe Tyr Arg Asn Ala Pro Thr Leu His Ile Glu Thr Val Asp Ser
            35                  40                  45

Asn Lys Glu Trp Thr Thr Ser Asp Ile Glu Val Thr Tyr Lys Pro Asn
 50                  55                  60

Phe Phe Val Gly Ser Ser Tyr Val Glu Phe Asn Phe Pro Tyr Arg Phe
65                  70                  75                  80

His Ala Asn Thr Arg Asp Ser Leu Asn Gly Arg Thr Leu Asn Tyr Thr
            85                  90                  95

Gln Ile Leu Asn Asp Gly Gln Thr Val Arg Val Pro Val Tyr Ala Phe
            100                 105                 110

Ser Ser Ser Glu Phe Lys Leu Val Met Val Arg Lys Thr Leu Pro Asn
            115                 120                 125

Ala Gly Thr His Arg Ile Thr Ala Glu Leu Gln Lys Phe Gly Arg Asn
            130                 135                 140

Tyr Asn His Ala Glu Ala Thr Val Asp Ile Leu Pro Arg
145                 150                 155

<210> SEQ ID NO 8
<211> LENGTH: 160
<212> TYPE: PRT
<213> ORGANISM: Bacillus licheniformis

<400> SEQUENCE: 8

Met Lys Thr Asn His Phe Arg Gly Pro Ile Phe Cys Pro Pro Pro Phe
1               5                   10                  15

Lys Pro Ala Pro Lys Pro Gln Pro Pro Gln Lys Pro Gln Pro Asp Asn
            20                  25                  30

Pro Gln Pro Asp Asn Pro Thr Gln Lys Pro Val Leu Glu Ala Lys Thr
            35                  40                  45

Ile Asn Ser Asn Lys Glu Trp Ser Thr Ser Asp Ile Glu Ile Thr Tyr
 50                  55                  60

Arg Pro Asn Ala Phe Val Gly Ser Ser Tyr Val Glu Phe His Phe Pro
65                  70                  75                  80

Tyr Arg Phe His Ala Ser Thr Arg Asp Thr Leu Asn Gly Lys Thr Leu
            85                  90                  95

Asp Tyr Thr Gln Ile Leu Asn Asp Gly Gln Thr Val Arg Val Pro Val
            100                 105                 110

Tyr Ala Leu Ser Ser Ser Glu Phe Lys Leu Val Met Val Arg Lys Thr
            115                 120                 125

Leu Pro Asn Ala Gly Thr His Arg Ile Thr Ala Glu Leu Gln Gln Asn
            130                 135                 140

Gly Lys Asn Ile Asn His Ala Glu Thr Thr Leu Glu Ile Val Pro Arg
145                 150                 155                 160

<210> SEQ ID NO 9
<211> LENGTH: 157
<212> TYPE: PRT
<213> ORGANISM: Bacillus licheniformis

<400> SEQUENCE: 9

Met Leu Lys Arg Lys Phe Ile Gly Lys Ile Gly Val Gly Leu Leu Thr
1               5                   10                  15

Ser Ala Ala Leu Phe Ser Phe Ile Leu Pro Thr Glu Glu Ala Ser Ala
            20                  25                  30
```

Thr Phe Tyr Arg Asn Ala Pro Thr Leu His Val Glu Thr Val Asp Ser
                 35                  40                  45

Asn Lys Glu Trp Thr Thr Ser Asp Ile Glu Val Thr Tyr Lys Pro Asn
 50                  55                  60

Phe Phe Val Gly Ser Ser Tyr Val Glu Phe Asn Phe Pro Tyr Arg Phe
 65                  70                  75                  80

His Ala Asn Thr Arg Asp Ser Leu Asn Gly Arg Thr Leu Asn Tyr Thr
                 85                  90                  95

Gln Ile Leu Asn Asp Gly Gln Thr Val Arg Val Pro Val Tyr Ala Phe
                100                 105                 110

Ser Ser Ser Glu Phe Lys Leu Val Met Val Arg Lys Thr Leu Pro Asn
                115                 120                 125

Ala Gly Thr His Arg Ile Thr Ala Glu Leu Gln Lys Phe Gly Arg Asn
                130                 135                 140

Tyr Asn His Ala Glu Ala Thr Val Asp Ile Leu Pro Arg
145                 150                 155

<210> SEQ ID NO 10
<211> LENGTH: 194
<212> TYPE: PRT
<213> ORGANISM: Bacillus licheniformis

<400> SEQUENCE: 10

Met Leu Lys Arg Lys Phe Ile Arg Lys Ile Ser Val Gly Leu Leu Ala
 1               5                  10                  15

Ser Ala Ala Leu Phe Ser Phe Ile Ile Pro Thr Gln Gly Ala Asn Ala
                 20                  25                  30

Gln Glu Val Lys Thr Asn His Phe Arg Gly Pro Ile Phe Cys Pro Pro
                 35                  40                  45

Pro Phe Lys Pro Ala Pro Lys Pro Gln Pro Pro Gln Lys Pro Gln Pro
 50                  55                  60

Asp Asn Pro Gln Pro Asp Asn Pro Thr Gln Lys Pro Val Leu Glu Ala
 65                  70                  75                  80

Lys Thr Ile Asn Ser Asn Lys Glu Trp Ser Thr Ser Asp Ile Glu Ile
                 85                  90                  95

Thr Tyr Arg Pro Asn Ala Phe Val Gly Ser Ser Tyr Val Glu Phe His
                100                 105                 110

Phe Pro Tyr Arg Phe His Ala Ser Thr Arg Asp Thr Leu Asn Gly Lys
                115                 120                 125

Thr Leu Asp Tyr Thr Gln Ile Leu Asn Asp Gly Gln Thr Val Arg Val
                130                 135                 140

Pro Val Tyr Ala Leu Ser Ser Ser Glu Phe Lys Leu Val Met Val Arg
145                 150                 155                 160

Lys Thr Leu Pro Asn Ala Gly Thr His Arg Ile Thr Ala Glu Leu Gln
                165                 170                 175

Gln Asn Gly Lys Asn Ile Asn His Ala Glu Thr Thr Leu Glu Ile Val
                180                 185                 190

Pro Arg

<210> SEQ ID NO 11
<211> LENGTH: 194
<212> TYPE: PRT
<213> ORGANISM: Bacillus licheniformis

<400> SEQUENCE: 11

Met Leu Lys Arg Lys Phe Ile Arg Lys Ile Ser Val Gly Leu Leu Ala

-continued

```
1               5                   10                  15
Ser Ala Ala Leu Phe Ser Phe Ile Ile Pro Thr Gln Gly Ala Asn Ala
                20                  25                  30
Gln Glu Val Lys Thr Asn His Phe Arg Gly Pro Ile Phe Cys Pro Pro
                35                  40                  45
Pro Phe Lys Pro Ser Pro Lys Pro Gln Pro Pro Gln Lys Pro Gln Pro
            50                  55                  60
Asp Asn Pro Gln Pro Asp Asn Pro Thr Gln Lys Pro Val Leu Glu Ala
 65                 70                  75                  80
Lys Thr Ile Asn Ser Asn Lys Glu Trp Ser Thr Ser Asp Ile Glu Ile
                85                  90                  95
Thr Tyr Arg Pro Asn Ser Phe Val Gly Ser Ser Tyr Val Glu Phe His
            100                 105                 110
Phe Pro Tyr Arg Phe His Ala Ser Thr Arg Asp Thr Leu Asn Gly Lys
            115                 120                 125
Thr Leu Asp Tyr Thr Gln Ile Leu Asn Asp Gly Gln Thr Val Arg Val
            130                 135                 140
Pro Val Tyr Ala Leu Ser Ser Ser Glu Phe Lys Leu Val Met Val Arg
145                 150                 155                 160
Lys Thr Leu Pro Asn Ala Gly Thr His Arg Ile Thr Ala Glu Leu Gln
                165                 170                 175
Gln Asn Gly Lys Asn Ile Asn His Ala Glu Thr Thr Leu Glu Ile Val
                180                 185                 190
Pro Arg
```

<210> SEQ ID NO 12
<211> LENGTH: 192
<212> TYPE: PRT
<213> ORGANISM: Bacillus glycinifermentans

<400> SEQUENCE: 12

```
Met Leu Lys Arg Lys Ile Ile Ser Lys Ile Ser Ile Gly Leu Leu Thr
 1                5                  10                  15
Ser Ala Ala Leu Phe Ser Phe Ile Leu Pro Thr Asn Glu Ala Asn Ala
                20                  25                  30
Gln Glu Val Asn Thr Ser His Phe Arg Gly Pro Ile Phe Cys Pro Pro
                35                  40                  45
Pro Phe Lys Pro Lys Pro Gln Pro Pro Gln Asn Pro Lys Pro Asp Asn
            50                  55                  60
Pro Leu Pro Asp Asn Pro Thr Gln Lys Pro Val Leu Glu Val Lys Ala
 65                 70                  75                  80
Val Asn Ser Asn Lys Glu Trp Thr Thr Ser Asp Ile Glu Ile Thr Tyr
                85                  90                  95
Lys Pro Asn Thr Phe Val Gly Thr Ser Tyr Val Glu Phe Asn Phe Pro
            100                 105                 110
Tyr Arg Phe His Ala Ser Thr Arg Asp Thr Leu Asn Gly Lys Thr Leu
            115                 120                 125
Asp Tyr Thr Gln Ile Leu Asn Asp Gly Gln Thr Val Arg Val Pro Val
            130                 135                 140
Tyr Ala Leu Ser Ser Ser Glu Phe Lys Leu Val Met Val Arg Lys Thr
145                 150                 155                 160
Leu Pro Asn Ala Gly Thr His Arg Ile Thr Ala Glu Leu Gln Gln Asn
                165                 170                 175
Gly Lys Asn Ile Asn His Ala Glu Ala Thr Leu Glu Ile Val Pro Arg
```

```
                      180             185             190
```

<210> SEQ ID NO 13
<211> LENGTH: 157
<212> TYPE: PRT
<213> ORGANISM: Bacillus glycinifermentans

<400> SEQUENCE: 13

```
Met Leu Lys Arg Lys Phe Ile Gly Lys Met Ser Val Gly Leu Leu Ala
1               5                   10                  15

Ser Ala Ala Leu Phe Ser Phe Ile Leu Pro Ser Gln Glu Ala Asn Ala
            20                  25                  30

Ala Phe Tyr Arg Ser Glu Pro Ala Leu His Val Glu Thr Thr Gln Ser
        35                  40                  45

Asn Lys Glu Trp Thr Thr Ser Asp Ile Glu Val Thr Tyr Lys Pro Asn
    50                  55                  60

Met Phe Val Gly Ala Ser Phe Val Glu Phe Asn Phe Pro Tyr Arg Phe
65                  70                  75                  80

His Ala Asp Thr Arg Asp Ser Leu Asn Gly Arg Thr Leu Asn Tyr Thr
                85                  90                  95

Gln Ile Leu Asn Asp Gly Gln Thr Val Arg Val Pro Val Tyr Ala Phe
            100                 105                 110

Ser Ser Ser Gln Phe Lys Leu Val Met Val Arg Lys Thr Leu Pro Asn
        115                 120                 125

Ala Gly Thr His Arg Ile Thr Ala Glu Leu Gln Lys Trp Gly Arg Asn
    130                 135                 140

Tyr Gly His Ala Glu Thr Met Val Glu Ile Ala Pro Arg
145                 150                 155
```

<210> SEQ ID NO 14
<211> LENGTH: 192
<212> TYPE: PRT
<213> ORGANISM: Bacillus glycinifermentans

<400> SEQUENCE: 14

```
Met Leu Lys Arg Lys Ile Ile Ser Lys Ile Ser Ile Gly Leu Leu Thr
1               5                   10                  15

Ser Ala Ala Leu Phe Ser Phe Ile Leu Pro Thr Asn Glu Ala Asn Ala
            20                  25                  30

Gln Glu Val Ser Thr Ser His Phe Arg Gly Pro Ile Phe Cys Pro Pro
        35                  40                  45

Pro Phe Lys Pro Lys Pro Gln Pro Pro Gln Tyr Pro Lys Pro Asp Asn
    50                  55                  60

Pro Leu Pro Asp Asn Pro Thr Gln Lys Pro Val Leu Glu Val Lys Ala
65                  70                  75                  80

Val Asn Ser Asn Lys Glu Trp Thr Thr Ser Asp Ile Glu Ile Thr Tyr
                85                  90                  95

Lys Pro Asn Thr Phe Val Gly Ser Tyr Val Glu Phe Asn Phe Pro
            100                 105                 110

Tyr Arg Phe His Ala Ser Thr Arg Asp Thr Leu Asn Gly Lys Thr Leu
        115                 120                 125

Asp Tyr Thr Gln Ile Leu Asn Asp Gly Gln Thr Val Arg Val Pro Val
    130                 135                 140

Tyr Ala Leu Ser Ser Ser Glu Phe Lys Leu Val Met Val Arg Lys Thr
145                 150                 155                 160

Leu Pro Asn Ala Gly Thr His Arg Ile Thr Ala Glu Leu Gln Gln Asn
```

```
                    165                 170                 175

Gly Lys Asn Ile Asn His Ala Glu Ala Thr Leu Glu Ile Val Pro Arg
                180                 185                 190

<210> SEQ ID NO 15
<211> LENGTH: 157
<212> TYPE: PRT
<213> ORGANISM: Bacillus glycinifermentans

<400> SEQUENCE: 15

Met Leu Lys Arg Lys Phe Ile Gly Lys Met Arg Val Gly Leu Leu Ala
1               5                   10                  15

Ser Ala Ala Leu Phe Ser Phe Ile Leu Pro Ser Gln Glu Ala Asn Ala
                20                  25                  30

Ala Phe Tyr Arg Ser Glu Pro Ala Leu His Val Glu Thr Thr Gln Ser
            35                  40                  45

Asn Lys Glu Trp Thr Thr Ser Asp Ile Glu Val Thr Tyr Lys Pro Asn
        50                  55                  60

Met Phe Val Gly Ala Ser Tyr Val Glu Phe Asn Phe Pro Tyr Arg Phe
65                  70                  75                  80

His Ala Asn Thr Arg Asp Ser Leu Asn Gly Arg Thr Leu Asn Tyr Thr
                85                  90                  95

Gln Ile Leu Asn Asp Gly Gln Thr Val Arg Val Pro Val Tyr Ala Phe
            100                 105                 110

Ser Ser Ser Gln Phe Lys Leu Val Met Val Arg Lys Thr Leu Pro Asn
        115                 120                 125

Ala Gly Thr His Arg Ile Thr Ala Glu Leu Gln Lys Trp Gly Arg Asn
    130                 135                 140

Tyr Gly His Ala Glu Thr Thr Val Glu Ile Ala Pro Arg
145                 150                 155

<210> SEQ ID NO 16
<211> LENGTH: 157
<212> TYPE: PRT
<213> ORGANISM: Bacillus sonorensis

<400> SEQUENCE: 16

Met Leu Lys Arg Asn Ile Ile Ser Lys Ile Ser Ile Gly Leu Leu Thr
1               5                   10                  15

Ser Ala Ala Leu Phe Ser Phe Ile Leu Pro Ser Gln Glu Ala His Ala
                20                  25                  30

Thr Phe Phe Arg Ser Glu Pro Thr Leu His Val Glu Thr Val Asp Ser
            35                  40                  45

Asn Lys Glu Trp Thr Thr Ser Asp Ile Glu Val Thr Tyr Lys Pro Asn
        50                  55                  60

Phe Phe Val Gly Ala Ser Tyr Val Glu Phe Asn Phe Pro Tyr Arg Phe
65                  70                  75                  80

His Ala Asn Thr Arg Asp Ser Leu Asn Gly Arg Thr Leu Asn Tyr Thr
                85                  90                  95

Gln Ile Leu Asn Asp Gly Gln Thr Val Arg Val Pro Val Tyr Ala Phe
            100                 105                 110

Ser Ser Ser Gln Phe Lys Leu Val Met Val Arg Lys Thr Leu Pro Asn
        115                 120                 125

Ala Gly Thr His Arg Val Thr Ala Glu Leu Gln Lys Phe Gly Arg His
    130                 135                 140

Tyr His His Ala Glu Ala Thr Val Glu Ile Ala Pro Arg
```

<210> SEQ ID NO 17
<211> LENGTH: 178
<212> TYPE: PRT
<213> ORGANISM: Bacillus paralicheniformis

<400> SEQUENCE: 17

```
Met Met Asn Leu Phe Phe Pro Phe Ser Ser Phe Leu Thr Thr Phe Ile
1               5                   10                  15
Arg Arg Gly Lys Tyr Met Leu Lys Arg Lys Phe Ile Gly Lys Met Gly
                20                  25                  30
Val Gly Leu Leu Thr Ser Ala Ala Leu Phe Ser Phe Ile Leu Pro Thr
            35                  40                  45
Glu Glu Ala Ser Ala Thr Phe Phe Arg Asn Ala Pro Thr Leu His Val
        50                  55                  60
Glu Thr Val Asp Ser Asn Lys Glu Trp Thr Thr Ser Asp Ile Glu Val
65                  70                  75                  80
Thr Tyr Lys Pro Asn Ser Phe Val Gly Ala Ser Tyr Val Glu Phe Asn
                85                  90                  95
Phe Pro Tyr Arg Phe His Ala Asn Thr Arg Asp Ser Leu Asn Gly Arg
            100                 105                 110
Thr Leu Asn Tyr Thr Gln Ile Leu Asn Asp Gly Gln Thr Val Arg Val
        115                 120                 125
Pro Val Tyr Ala Phe Ser Ser Ala Phe Lys Leu Val Met Val Arg
        130                 135                 140
Lys Thr Leu Pro Asn Ala Gly Thr His Arg Val Thr Ala Glu Leu Gln
145                 150                 155                 160
Lys Phe Gly Arg Asn Tyr Asn His Ala Glu Ala Thr Val Asp Ile Leu
                165                 170                 175
Pro Arg
```

<210> SEQ ID NO 18
<211> LENGTH: 194
<212> TYPE: PRT
<213> ORGANISM: Bacillus paralicheniformis

<400> SEQUENCE: 18

```
Met Leu Lys Arg Lys Phe Ile Arg Lys Ile Ser Val Ala Leu Leu Ala
1               5                   10                  15
Ser Ala Ala Leu Phe Ser Phe Ile Ile Pro Thr Gln Gly Ala Asn Ala
                20                  25                  30
Gln Glu Val Lys Thr Asn His Phe Arg Gly Pro Ile Phe Cys Pro Pro
            35                  40                  45
Pro Phe Lys Pro Trp Pro Lys Pro Gln Pro Pro Gln Lys Pro Gln Pro
        50                  55                  60
Asp Tyr Pro Gln Pro Asp Asn Pro Thr Gln Lys Pro Val Leu Glu Ala
65                  70                  75                  80
Lys Thr Ile Asn Ser Asn Lys Glu Trp Ser Thr Ser Asp Ile Glu Ile
                85                  90                  95
Thr Tyr Lys Pro Asn Thr Phe Val Gly Ser Ser Tyr Val Glu Phe His
            100                 105                 110
Phe Pro Tyr Arg Phe His Ala Ser Thr Arg Asp Thr Leu Asn Gly Lys
        115                 120                 125
Thr Leu Asp Tyr Thr Gln Ile Leu Asn Asp Gly Gln Thr Val Arg Val
        130                 135                 140
```

Pro Val Tyr Ala Leu Ser Ser Glu Phe Lys Leu Val Met Val Arg
145                 150                 155                 160

Lys Thr Leu Pro Asn Ala Gly Thr His Arg Ile Thr Ala Glu Leu Gln
            165                 170                 175

Gln Asn Gly Lys Asn Ile Asn His Ala Glu Thr Thr Leu Glu Ile Val
        180                 185                 190

Pro Arg

<210> SEQ ID NO 19
<211> LENGTH: 157
<212> TYPE: PRT
<213> ORGANISM: Bacillus sp. NRRL B-41282

<400> SEQUENCE: 19

Met Phe Lys Arg Lys Phe Val Gly Lys Leu Gly Val Gly Leu Leu Ser
1               5                   10                  15

Ser Ala Leu Leu Ser Phe Ile Leu Pro Ala Gln Glu Ala Ser Ala
            20                  25                  30

Thr Phe Phe Arg Ser Ala Pro Thr Leu His Val Glu Thr Val Asp Ser
        35                  40                  45

Asn Lys Glu Trp Thr Thr Ser Asp Ile Glu Val Thr Tyr Lys Pro Asn
50                  55                  60

Ser Phe Val Gly Ser Ser Tyr Val Glu Phe Asn Phe Pro Tyr Arg Phe
65                  70                  75                  80

His Ala Asn Thr Arg Asp Ser Leu Asn Gly Arg Thr Leu Asn Tyr Thr
                85                  90                  95

Gln Ile Leu Asn Asp Gly Gln Thr Val Arg Val Pro Val Tyr Ala Phe
            100                 105                 110

Ser Ser Ser Gln Phe Lys Leu Val Met Val Arg Lys Thr Leu Pro Asn
        115                 120                 125

Ala Gly Thr His Lys Ile Thr Ala Glu Leu Gln Lys Phe Gly Arg Asn
    130                 135                 140

Tyr Asn His Ala Glu Thr Thr Val Glu Ile Val Pro Arg
145                 150                 155

<210> SEQ ID NO 20
<211> LENGTH: 185
<212> TYPE: PRT
<213> ORGANISM: Bacillus sp. NRRL B-41282

<400> SEQUENCE: 20

Met Phe Lys Arg Lys Phe Ile Arg Lys Leu Ser Val Gly Leu Leu Thr
1               5                   10                  15

Ser Ala Ala Leu Phe Ser Phe Ile Leu Pro Thr Ser Gly Ala Ser Ala
            20                  25                  30

Gln Glu Val Asn Thr Lys His Phe Arg Gly Pro Ile Phe Cys Pro Pro
        35                  40                  45

Pro His Trp Pro Lys Lys Pro Gln Lys Pro Asp Asp Pro Thr
50                  55                  60

Lys Gln Pro Val Leu Glu Ala Lys Thr Ile Asn Ser Asn Lys Glu Trp
65                  70                  75                  80

Thr Thr Ser Asp Ile Glu Ile Thr Tyr Lys Pro Asn Thr Phe Val Gly
                85                  90                  95

Ser Ser Tyr Val Glu Phe His Pro Tyr Arg Phe His Ala Ser Thr
            100                 105                 110

Arg Asp Thr Leu Asn Gly Lys Ala Leu Glu Tyr Thr Gln Ile Leu Asn
                115                 120                 125

Asp Gly Gln Thr Val Arg Val Pro Val Tyr Ala Leu Ser Ser Ser Glu
            130                 135                 140

Phe Lys Leu Val Met Ile Arg Lys Thr Leu Pro Asn Ala Gly Thr His
145                 150                 155                 160

Arg Ile Thr Ala Glu Leu His Gln Asn Gly Lys Asn Ile Asn His Ala
                165                 170                 175

Glu Thr Thr Leu Glu Ile Val Pro Arg
                180                 185

<210> SEQ ID NO 21
<211> LENGTH: 157
<212> TYPE: PRT
<213> ORGANISM: Bacillus sp. NRRL B-41327

<400> SEQUENCE: 21

Met Leu Lys Arg Lys Phe Ile Gly Lys Met Gly Val Gly Leu Leu Thr
1               5                   10                  15

Ser Ala Ala Leu Phe Ser Phe Ile Leu Pro Thr Glu Glu Ala Ser Ala
                20                  25                  30

Thr Phe Tyr Arg Asn Ala Pro Thr Leu His Val Glu Thr Val Asp Ser
            35                  40                  45

Asn Lys Glu Trp Thr Thr Ser Asp Ile Glu Val Thr Tyr Lys Pro Asn
50                  55                  60

Ser Phe Val Gly Ser Ser Tyr Val Glu Phe Asn Phe Pro Tyr Arg Phe
65                  70                  75                  80

His Ala Asn Thr Arg Asp Ser Leu Asn Gly Arg Thr Leu Ser Tyr Thr
                85                  90                  95

Gln Ile Leu Asn Asp Gly Gln Thr Val Arg Val Pro Val Tyr Ala Phe
                100                 105                 110

Ser Ser Ser Glu Phe Lys Leu Val Met Val Arg Lys Thr Leu Pro Asn
            115                 120                 125

Ala Gly Thr His Arg Ile Thr Ala Glu Leu Gln Lys Phe Gly Arg Asn
            130                 135                 140

Tyr Asn His Ala Glu Thr Thr Val Asp Ile Leu Pro Arg
145                 150                 155

<210> SEQ ID NO 22
<211> LENGTH: 194
<212> TYPE: PRT
<213> ORGANISM: Bacillus sp. NRRL B-41327

<400> SEQUENCE: 22

Met Leu Lys Arg Lys Phe Ile Arg Lys Ile Ser Val Gly Leu Leu Ala
1               5                   10                  15

Ser Ala Ala Leu Phe Ser Phe Ile Ile Pro Thr Gln Gly Ala Asn Ala
                20                  25                  30

Gln Glu Val Lys Thr Asn His Phe Arg Gly Pro Ile Phe Cys Pro Pro
            35                  40                  45

Pro Phe Lys Pro Ser Pro Lys Pro Gln Pro Gln Lys Pro Gln Pro
50                  55                  60

Asp Asn Pro Gln Ser Asp Asn Pro Thr Gln Lys Pro Val Leu Glu Ala
65                  70                  75                  80

Lys Thr Ile Asn Ser Asn Lys Glu Trp Ser Thr Ser Asp Ile Glu Ile
                85                  90                  95

```
Thr Tyr Arg Pro Asn Ser Phe Val Gly Ser Ser Tyr Val Glu Phe His
                100                 105                 110

Phe Pro Tyr Arg Phe His Ala Ser Thr Arg Asp Thr Leu Asn Gly Lys
            115                 120                 125

Thr Leu Asp Tyr Thr Gln Ile Leu Asn Asp Gly Gln Thr Val Arg Val
        130                 135                 140

Pro Val Tyr Ala Leu Ser Ser Ser Glu Phe Lys Leu Val Met Val Arg
145                 150                 155                 160

Lys Thr Leu Pro Asn Ala Gly Thr His Arg Ile Thr Ala Glu Leu Gln
                165                 170                 175

Gln Asn Gly Lys Asn Ile Asn His Ala Glu Thr Thr Leu Glu Ile Val
            180                 185                 190

Pro Arg

<210> SEQ ID NO 23
<211> LENGTH: 110
<212> TYPE: PRT
<213> ORGANISM: Artificial Sequence
<220> FEATURE:
<223> OTHER INFORMATION: Consensus protein sequence
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (44)..(45)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
```

```
<220> FEATURE:
<221> NAME/KEY: misc_feature
<222> LOCATION: (75)..(75)
<223> OTHER INFORMATION: Xaa can be any naturally occurring amino acid
<220> FEATURE:
<221> NAME/KEY: misc_feature
<222> LOCATION: (86)..(87)
<223> OTHER INFORMATION: Xaa can be any naturally occurring amino acid
<220> FEATURE:
<221> NAME/KEY: misc_feature
<222> LOCATION: (92)..(94)
<223> OTHER INFORMATION: Xaa can be any naturally occurring amino acid
<220> FEATURE:
<221> NAME/KEY: misc_feature
<222> LOCATION: (96)..(99)
<223> OTHER INFORMATION: Xaa can be any naturally occurring amino acid
<220> FEATURE:
<221> NAME/KEY: misc_feature
<222> LOCATION: (103)..(106)
<223> OTHER INFORMATION: Xaa can be any naturally occurring amino acid
<220> FEATURE:
<221> NAME/KEY: misc_feature
<222> LOCATION: (108)..(108)
<223> OTHER INFORMATION: Xaa can be any naturally occurring amino acid

<400> SEQUENCE: 23

Ser Asn Lys Glu Trp Xaa Thr Ser Asp Ile Glu Xaa Thr Tyr Xaa Pro
1               5                   10                  15

Asn Xaa Phe Val Gly Xaa Ser Xaa Val Glu Phe Xaa Phe Pro Tyr Arg
            20                  25                  30

Phe His Ala Xaa Thr Arg Asp Xaa Leu Asn Gly Xaa Xaa Leu Xaa Tyr
        35                  40                  45

Thr Gln Ile Leu Asn Asp Gly Gln Thr Val Arg Val Pro Val Tyr Ala
    50                  55                  60

Xaa Ser Ser Ser Xaa Phe Lys Leu Val Met Xaa Arg Lys Thr Leu Pro
65                  70                  75                  80

Asn Ala Gly Thr His Xaa Xaa Thr Ala Glu Leu Xaa Xaa Xaa Gly Xaa
                85                  90                  95

Xaa Xaa Xaa His Ala Glu Xaa Xaa Xaa Xaa Ile Xaa Pro Arg
            100                 105                 110

<210> SEQ ID NO 24
<211> LENGTH: 141
<212> TYPE: PRT
<213> ORGANISM: Thermoactinomyces vulgaris

<400> SEQUENCE: 24

Asn Pro Pro Ala Pro Ala Asp Ala Glu Val Pro Ser Lys Trp Gln Ala
1               5                   10                  15

Ala Gln Gly Lys Ala Leu Thr Val Arg Leu Glu Pro Ser Lys Asn Lys
            20                  25                  30

Gln Glu Ala Val Ser Asp Val Val Ile Thr Tyr Lys Pro Asp Val Val
        35                  40                  45

Leu Ala Tyr Gly Arg Ala Lys Phe His Leu Pro Lys Gly Phe Ser Ala
    50                  55                  60

Val Ala Gly Asp Leu Ile Asn Gly Gln Pro Leu Thr Ala Asp Tyr Ile
65                  70                  75                  80

Gln Asn Gly Gly Gln Thr Val Thr Leu Pro Phe Gly Val Asp Ile Gly
                85                  90                  95

Ala Met Arg Ile Phe Glu Leu Arg Leu Val Gly Lys Lys Leu Pro Ser
            100                 105                 110

Ala Gly Gln Tyr Lys Phe Arg Ala Glu Tyr Trp Gly Ile Gly Ile Gly
        115                 120                 125
```

Ile Tyr Asn Thr Ala Glu Ala Val Leu Glu Leu Arg Asn
    130                 135                 140

<210> SEQ ID NO 25
<211> LENGTH: 423
<212> TYPE: DNA
<213> ORGANISM: Artificial Sequence
<220> FEATURE:
<223> OTHER INFORMATION: codon optimized artificial DNA sequence

<400> SEQUENCE: 25

```
aacccgccgg cgccggcgga tgcggaagtg ccgagcaagt ggcaagcggc gcagggtaaa      60
gcgctgaccg tgcgtctgga gccgagcaag aacaaacagg aagcggttag cgacgtggtt     120
attacctaca agccggatgt ggttctggcg tatggccgtg cgaagttcca cctgccgaaa     180
ggttttagcg cggttgcggg cgacctgatt aacggtcaac cgctgaccgc ggattacatc     240
cagaacggtg gccaaaccgt gaccctgccg ttcggcgttg atattggtgc gatgcgtatc     300
tttgagctgc gtctggtggg caagaaactg ccgagcgcgg ccagtacaa attccgtgcg     360
gaatattggg gtatcggcat tggtatctat aacaccgcgg aggcggttct ggaactgcgt     420
aac                                                                  423
```

<210> SEQ ID NO 26
<211> LENGTH: 155
<212> TYPE: PRT
<213> ORGANISM: Thermoactinomyces vulgaris

<400> SEQUENCE: 26

Met His His His His His Glu Asn Leu Tyr Phe Gln Gly Asn Pro
1               5                   10                  15

Pro Ala Pro Ala Asp Ala Glu Val Pro Ser Lys Trp Gln Ala Gln
            20                  25                  30

Gly Lys Ala Leu Thr Val Arg Leu Glu Pro Ser Lys Asn Lys Gln Glu
        35                  40                  45

Ala Val Ser Asp Val Val Ile Thr Tyr Lys Pro Asp Val Val Leu Ala
    50                  55                  60

Tyr Gly Arg Ala Lys Phe His Leu Pro Lys Gly Phe Ser Ala Val Ala
65                  70                  75                  80

Gly Asp Leu Ile Asn Gly Gln Pro Leu Thr Ala Asp Tyr Ile Gln Asn
                85                  90                  95

Gly Gly Gln Thr Val Thr Leu Pro Phe Gly Val Asp Ile Gly Ala Met
            100                 105                 110

Arg Ile Phe Glu Leu Arg Leu Val Gly Lys Lys Leu Pro Ser Ala Gly
        115                 120                 125

Gln Tyr Lys Phe Arg Ala Glu Tyr Trp Gly Ile Gly Ile Gly Ile Tyr
    130                 135                 140

Asn Thr Ala Glu Ala Val Leu Glu Leu Arg Asn
145                 150                 155

<210> SEQ ID NO 27
<211> LENGTH: 417
<212> TYPE: DNA
<213> ORGANISM: Artificial Sequence
<220> FEATURE:
<223> OTHER INFORMATION: codon optimized artificial DNA sequence

<400> SEQUENCE: 27

```
atgcatcatc accatcacca cgaaaacctg tattttcagg gcaccttcta ccgtaacgcg      60
```

```
ccgaccctgc acatcgagac cgttgacagc aacaaggaat ggaccaccag cgatattgag    120
gtgacctata aaccgaactt ctttgttggt agcagctacg tggaattcaa ctttccgtat    180
cgttttcacg cgaacacccg tgacagcctg aacggtcgta ccctgaacta cacccagatc    240
ctgaacgatg gccaaaccgt gcgtgttccg gtgtatgcgt tcagcagcag cgagtttaag    300
ctggttatgg tgcgtaaaac cctgccgaac gcgggtaccc accgtatcac cgcggaactg    360
cagaagttcg gccgtaacta caaccacgcg gaggcgaccg ttgacattct gccgcgt      417
```

<210> SEQ ID NO 28
<211> LENGTH: 139
<212> TYPE: PRT
<213> ORGANISM: Bacillus licheniformis

<400> SEQUENCE: 28

```
Met His His His His His His Glu Asn Leu Tyr Phe Gln Gly Thr Phe
1               5                   10                  15

Tyr Arg Asn Ala Pro Thr Leu His Ile Glu Thr Val Asp Ser Asn Lys
            20                  25                  30

Glu Trp Thr Thr Ser Asp Ile Glu Val Thr Tyr Lys Pro Asn Phe Phe
        35                  40                  45

Val Gly Ser Ser Tyr Val Glu Phe Asn Phe Pro Tyr Arg Phe His Ala
    50                  55                  60

Asn Thr Arg Asp Ser Leu Asn Gly Arg Thr Leu Asn Tyr Thr Gln Ile
65                  70                  75                  80

Leu Asn Asp Gly Gln Thr Val Arg Val Pro Val Tyr Ala Phe Ser Ser
                85                  90                  95

Ser Glu Phe Lys Leu Val Met Val Arg Lys Thr Leu Pro Asn Ala Gly
            100                 105                 110

Thr His Arg Ile Thr Ala Glu Leu Gln Lys Phe Gly Arg Asn Tyr Asn
        115                 120                 125

His Ala Glu Ala Thr Val Asp Ile Leu Pro Arg
    130                 135
```

<210> SEQ ID NO 29
<211> LENGTH: 417
<212> TYPE: DNA
<213> ORGANISM: Artificial Sequence
<220> FEATURE:
<223> OTHER INFORMATION: codon optimized artificial DNA sequence

<400> SEQUENCE: 29

```
cgtacccaaa gcaccgcgag cctgtttgcg accatcaccg cgcgagcaa gaccgagtgg     60 agcttcagcg acattgaact gacctatcgt ccgaacaccc tgctgagcct gggtgtgatg    120
gagttcaccc tgccgagcgg ctttaccgcg aacaccaagg acaccctgaa cggtaacgcg    180
ctgcgtacca cccagatcct gaacaacggc aaaaccgtgc gtgttccgct ggcgctggat    240
ctgctgggtg cgggtgaatt taagctgaaa ctgaacaaca gaccctgcc ggcggcgggt    300 acctacacct tccgtgcgga gaacaagagc ctgagcatcg caacaaatt ttatgcggaa    360 gcgagcattg atgttgcgaa gcgtagcacc ccgccgaccc aaccgtgcgg ttgcaac      417
```

<210> SEQ ID NO 30
<211> LENGTH: 153
<212> TYPE: PRT
<213> ORGANISM: Bacillus subtilis

<400> SEQUENCE: 30

```
Met His His His His His Glu Asn Leu Tyr Phe Gln Gly Arg Thr
1               5                   10                  15

Gln Ser Thr Ala Ser Leu Phe Ala Thr Ile Thr Gly Ala Ser Lys Thr
            20                  25                  30

Glu Trp Ser Phe Ser Asp Ile Glu Leu Thr Tyr Arg Pro Asn Thr Leu
            35                  40                  45

Leu Ser Leu Gly Val Met Glu Phe Thr Leu Pro Ser Gly Phe Thr Ala
50                  55                  60

Asn Thr Lys Asp Thr Leu Asn Gly Asn Ala Leu Arg Thr Thr Gln Ile
65              70                  75                  80

Leu Asn Asn Gly Lys Thr Val Arg Val Pro Leu Ala Leu Asp Leu Leu
                85                  90                  95

Gly Ala Gly Glu Phe Lys Leu Lys Leu Asn Asn Lys Thr Leu Pro Ala
                100                 105                 110

Ala Gly Thr Tyr Thr Phe Arg Ala Glu Asn Lys Ser Leu Ser Ile Gly
            115                 120                 125

Asn Lys Phe Tyr Ala Glu Ala Ser Ile Asp Val Ala Lys Arg Ser Thr
130                 135                 140

Pro Pro Thr Gln Pro Cys Gly Cys Asn
145                 150

<210> SEQ ID NO 31
<211> LENGTH: 366
<212> TYPE: DNA
<213> ORGANISM: Artificial Sequence
<220> FEATURE:
<223> OTHER INFORMATION: codon optimized artificial DNA sequence

<400> SEQUENCE: 31
gcggtgatcg aggcgaagac cgttaacagc accaaagagt acgcgaccag cgacattgaa      60
gtgacctata aaccgaacgc gctgctggcg gtgggtgcgg ttgagttcca gtttccggac     120
ggtttcaacg cgaccgtgcg tgatagcgtt aacggccgta ccctgaagga aacccaaatc     180
ctgaactacg gtaaaaccgt tcgtctgccg ctgaccctgg acctgttcgg tgcgagcgag     240
tataacctgg tgctggttcg taagaacctg ccgcgtgcgg gcacctacac catcaagggt     300
gactatgtga acggtctggg tgcgggtagc ctgtatgcgg aaaccaaact ggttattgat     360
ccgcgt                                                                366

<210> SEQ ID NO 32
<211> LENGTH: 136
<212> TYPE: PRT
<213> ORGANISM: Bacillus velezensis

<400> SEQUENCE: 32

Met His His His His His Glu Asn Leu Tyr Phe Gln Gly Ala Val
1               5                   10                  15

Ile Glu Ala Lys Thr Val Asn Ser Thr Lys Glu Tyr Ala Thr Ser Asp
            20                  25                  30

Ile Glu Val Thr Tyr Lys Pro Asn Ala Leu Leu Ala Val Gly Ala Val
            35                  40                  45

Glu Phe Gln Phe Pro Asp Gly Phe Asn Ala Thr Val Arg Asp Ser Val
50                  55                  60

Asn Gly Arg Thr Leu Lys Glu Thr Gln Ile Leu Asn Tyr Gly Lys Thr
65              70                  75                  80

Val Arg Leu Pro Leu Thr Leu Asp Leu Phe Gly Ala Ser Glu Tyr Asn
```

-continued

```
                85                  90                  95
Leu Val Leu Val Arg Lys Asn Leu Pro Arg Ala Gly Thr Tyr Thr Ile
            100                 105                 110

Lys Gly Asp Tyr Val Asn Gly Leu Gly Ala Gly Ser Leu Tyr Ala Glu
            115                 120                 125

Thr Lys Leu Val Ile Asp Pro Arg
            130                 135
```